(12) United States Patent
Sung et al.

(10) Patent No.: US 8,454,966 B2
(45) Date of Patent: *Jun. 4, 2013

(54) NANOPARTICLES FOR PROTEIN DRUG DELIVERY

(75) Inventors: Hsing-Wen Sung, Hsinchu (TW); Yu-Hsin Lin, Kaohsiung (TW); Hsiang-Fa Liang, Hsinchu (TW); Hosheng Tu, Newport Beach, CA (US)

(73) Assignees: GP Medical, Inc., Newport Beach, CA (US); National Tsing Hua University, Hsinchu (TW)

( * ) Notice: Subject to any disclaimer, the term of this patent is extended or adjusted under 35 U.S.C. 154(b) by 308 days.

This patent is subject to a terminal disclaimer.

(21) Appl. No.: 12/807,084

(22) Filed: Aug. 27, 2010

(65) Prior Publication Data

US 2010/0330167 A1    Dec. 30, 2010

Related U.S. Application Data

(63) Continuation of application No. 11/881,217, filed on Jul. 26, 2007, now Pat. No. 7,803,748, which is a continuation of application No. 11/284,734, filed on Nov. 21, 2005, now Pat. No. 7,282,194, which is a continuation-in-part of application No. 11/029,082, filed on Jan. 4, 2005, now Pat. No. 7,265,090, which is a continuation-in-part of application No. 10/958,864, filed on Oct. 5, 2004, now Pat. No. 7,348,026.

(51) Int. Cl.
*A61K 38/14* (2006.01)
*A61K 31/715* (2006.01)
*A61K 47/36* (2006.01)

(52) U.S. Cl.
USPC ....... 424/184.1; 514/54; 424/278.1; 977/917; 977/773

(58) Field of Classification Search
None
See application file for complete search history.

(56) References Cited

U.S. PATENT DOCUMENTS

| | | | |
|---|---|---|---|
| 6,383,478 B1 * | 5/2002 | Prokop et al. | 424/78.08 |
| 7,858,596 B2 * | 12/2010 | Sung et al. | 514/55 |
| 7,988,949 B2 * | 8/2011 | Sung et al. | 424/1.69 |
| 2006/0293216 A1 | 12/2006 | Klaveness et al. | |
| 2007/0148251 A1 | 6/2007 | Hossainy et al. | |

OTHER PUBLICATIONS van der Lubben, 2001, European Journal of Pharmaceutical Sciences, 14, 201-207.*
Lin YH et al. "Relationship of nanoparticles composed of chitosan/poly-r-glutamic acid and evaluation of their permeability through Caco-2 cells" Biomacromo 2005;6:1104-12.
Lin YH et al. "Preparation and characterization of nanoparticles shelled with chitosan for oral insulin delivery" Biomacromolecules 2007;8:146-152.
Lin YH et al. "Novel nanoparticles for oral insulin delivery via the paracellular pathway" Nanotechnology 2007;18(105102):1-11.
van der Lubben IM et al. "Chitosan and its derivatives in mucosal drug and vaccine delivery" Eur J Pharma Sci 2001;14:201-207.
Thanou M et al. "Chitosan and its derivatives as intestinal absorption enhancers" Adv. Drug Deliv. Rev. 2001;50:S91-S101.
Smith J et al. "Effect of chitosan on epithelial cell tight junction" Pharma Res 2004;21(1):43-49.
Ma Z et al. "Formulation pH modulates the interaction of insulin with chitosan nanoparticles" J Pharma Sci 2002;91(6):1396-1404.
Vila A et al. "Low molecular weight chitosan nanoparticles as new carriers for nasal vaccine delivery in mice" Eur J Pharma and Biopharma 2004;57:123-131.

* cited by examiner

*Primary Examiner* — Satyanarayana R Gudibande

(57) ABSTRACT

The invention discloses the nanoparticles composed of chitosan, poly-γ-glutamic acid, and at least one bioactive agent characterized with a positive surface charge and their enhanced permeability for paracellular drug delivery.

15 Claims, 14 Drawing Sheets

(a)

(b)

MU : mucus
EC : enterocytes
MC : M cells
LC : lymphocytes
MP : macrophages
BL : basal lamina
TJ : tight junction

NANOPARTICLES FOR PROTEIN DRUG DELIVERY

CROSS-REFERENCE TO RELATED APPLICATIONS

This application is a continuation application of U.S. patent application Ser. No. 11/881,217, filed Jul. 26, 2007, now U.S. Pat. No. 7,803,748, which is a continuation application of U.S. patent application Ser. No. 11/284,734, filed Nov. 21, 2005, now U.S. Pat. No. 7,282,194, which is a continuation-in-part application of U.S. patent application Ser. No. 11/029,082, filed Jan. 4, 2005, now U.S. Pat. No. 7,265,090, which is a continuation-in-part application of U.S. patent application Ser. No. 10/958,864, filed Oct. 5, 2004, now U.S. Pat. No. 7,348,026, the entire contents of which are incorporated herein by reference.

FIELD OF THE INVENTION

The present invention is related to medical uses of nanoparticles composed of chitosan/poly-γ-glutamic acid with protein drugs and their permeability for enhanced paracellular drug delivery.

BACKGROUND OF THE INVENTION

Production of pharmaceutically active peptides and proteins in large quantities has become feasible (Biomacromolecules 2004; 5:1917-1925). The oral route is considered the most convenient way of drug administrations for patients. Nevertheless, the intestinal epithelium is a major barrier to the absorption of hydrophilic drugs such as peptides and proteins (J. Control. Release 1996; 39:131-138). This is because hydrophilic drugs cannot easily diffuse across the cells through the lipid-bilayer cell membranes. Attentions have been given to improving paracellular transport of hydrophilic drugs (J. Control. Release 1998; 51:35-46). The transport of hydrophilic molecules via the paracellular pathway is, however, severely restricted by the presence of tight junctions that are located at the luminal aspect of adjacent epithelial cells (Annu. Rev. Nutr. 1995; 15:35-55). These tight junctions form a barrier that limits the paracellular diffusion of hydrophilic molecules. The structure and function of tight junctions is described, inter alia, in Ann. Rev. Physiol. 1998; 60:121-160 and in Ballard T S et al., Annu. Rev. Nutr. 1995; 15:35-55. Tight junctions do not form a rigid barrier but play an important role in the diffusion through the intestinal epithelium from lumen to bloodstream and vice versa.

Movement of solutes between cells, through the tight junctions that bind cells together into a layer as with the epithelial cells of the gastrointestinal tract, is termed paracellular transport. Paracellular transport is passive. Paracellular transport depends on electrochemical gradients generated by transcellular transport and on solvent drag through tight junctions. Tight junctions form an intercellular barrier that separates the apical and basolateral fluid compartments of a cell layer. Movement of a solute through a tight junction from apical to basolateral compartments depends on the "tightness" of the tight junction for that solute.

Polymeric nanoparticles have been widely investigated as carriers for drug delivery (Biomaterials 2002; 23:3193-3201). Much attention has been given to the nanoparticles made of synthetic biodegradable polymers such as poly-ε-caprolactone and polylactide due to their good biocompatibility (J. Drug Delivery 2000; 7:215-232; Eur. J. Pharm. Biopharm. 1995; 41:19-25). However, these nanoparticles are not ideal carriers for hydrophilic drugs because of their hydrophobic property. Some aspects of the invention relate to a novel nanoparticle system, composed of hydrophilic chitosan and poly-γ-glutamic acid hydrogels that is prepared by a simple ionic-gelation method. This technique is promising as the nanoparticles are prepared under mild conditions without using harmful solvents. It is known that organic solvents may cause degradation of peptide or protein drugs that are unstable and sensitive to their environments (J. Control. Release 2001; 73:279-291).

Following the oral drug delivery route, protein drugs are readily degraded by the low pH of gastric medium in the stomach. The absorption of protein drugs following oral administration is challenging due to their high molecular weight, hydrophilicity, and susceptibility to enzymatic inactivation. Protein drugs at the intestinal epithelium could not partition into the hydrophobic membrane and thus can only traverse the epithelial barrier via the paracellular pathway. However, the tight junction forms a barrier that limits the paracellular diffusion of hydrophilic molecules.

Chitosan (CS), a cationic polysaccharide, is generally derived from chitin by alkaline deacetylation (J. Control. Release 2004; 96:285-300). It was reported from literature that CS is non-toxic and soft-tissue compatible (Biomacromolecules 2004; 5:1917-1925; Biomacromolecules 2004; 5:828-833). Additionally, it is known that CS has a special feature of adhering to the mucosal surface and transiently opening the tight junctions between epithelial cells (Pharm. Res. 1994; 11:1358-1361). Most commercially available CSs have a quite large molecular weight (MW) and need to be dissolved in an acetic acid solution at a pH value of approximately 4.0 or lower that is sometimes impractical. However, there are potential applications of CS in which a low MW would be essential. Given a low MW, the polycationic characteristic of CS can be used together with a good solubility at a pH value close to physiological ranges (Eur. J. Pharm. Biopharm. 2004; 57:101-105). Loading of peptide or protein drugs at physiological pH ranges would preserve their bioactivity. On this basis, a low-MW CS, obtained by depolymerizing a commercially available CS using cellulase, is disclosed herein to prepare nanoparticles of the present invention.

The γ-PGA, an anionic peptide, is a natural compound produced as capsular substance or as slime by members of the genus *Bacillus* (Crit. Rev. Biotechnol. 2001; 21:219-232). γ-PGA is unique in that it is composed of naturally occurring L-glutamic acid linked together through amide bonds. It was reported from literature that this naturally occurring γ-PGA is a water-soluble, biodegradable, and non-toxic polymer. A related, but structurally different polymer, [poly(α-glutamic acid), α-PGA] has been used for drug delivery (Adv. Drug Deliver. Rev. 2002; 54:695-713; Cancer Res. 1998; 58:2404-2409). α-PGA is usually synthesized from poly(γ-benzyl-L-glutamate) by removing the benzyl protecting group with the use of hydrogen bromide. Hashida et al. used α-PGA as a polymeric backbone and galactose moiety as a ligand to target hepatocytes (J. Control. Release 1999; 62:253-262). Their in vivo results indicated that the galactosylated α-PGA had a remarkable targeting ability to hepatocytes and degradation of α-PGA was observed in the liver.

Thanou et al. reported chitosan and its derivatives as intestinal absorption enhancers (Adv Drug Deliv Rev 2001; 50:S91-S101). Chitosan, when protonated at an acidic pH, is able to increase the paracellular permeability of peptide drugs across mucosal epithelia. Co-administration of chitosan or trimethyl chitosan chloride with peptide drugs were found to substantially increase the bioavailability of the peptide in animals compared with administrations without the chitosan component.

SUMMARY OF THE INVENTION

It is one object of the present invention to provide a novel nanoparticle system and methods of preparation for paracellular transport drug delivery using a simple and mild ionic-gelation method upon addition of a poly-γ-glutamic acid (γ-PGA) solution into a low molecular weight chitosan (low-MW CS) solution. In one embodiment, the molecular weight of a low-MW CS of the present invention is about 80 kDa or less, preferably at about 40 kDa, adapted for adequate solubility at a pH that maintains the bioactivity of protein and peptide drugs. It is stipulated that a chitosan particle with about 30-50 kDa molecular weight is kidney inert. The particle size and the zeta potential value of the prepared nanoparticles are controlled by their constituted compositions. The results obtained by the TEM (transmission electron microscopy) and AFM (atomic force microscopy) examinations showed that the morphology of the prepared nanoparticles was generally spherical in shape. Evaluation of the prepared nanoparticles in enhancing intestinal paracellular transport was investigated in vitro in Caco-2 cell monolayers. In some aspects of the present invention, it provides the nanoparticles with CS dominated on the surfaces to effectively reduce the transepithelial electrical resistance (TEER) of Caco-2 cell monolayers. The confocal laser scanning microscopy (CLSM) observations confirm that the nanoparticles with CS dominated on the surface are able to open the tight junctions between Caco-2 cells and allows transport of the nanoparticles via the paracellular pathways.

Some aspects of the invention relate to a method of enhancing intestinal or blood brain paracellular transport configured for delivering at least one bioactive agent in a patient comprising administering nanoparticles composed of γ-PGA and chitosan, wherein the step of administering the nanoparticles may be via oral administration. In one embodiment, the chitosan dominates on a surface of the nanoparticles. In another embodiment, a surface of the nanoparticles is characterized with a positive surface charge.

In a further embodiment, the chitosan of the nanoparticles is a low molecular weight chitosan, wherein the low molecular weight chitosan has a molecular weight of about 50 kDa, preferably having a molecular weight of less than about 40 kDa.

In a further embodiment, the nanoparticles have a mean particle size between about 50 and 400 nanometers, preferably between about 100 and 300 nanometers, and most preferably between about 100 and 200 nanometers.

In some embodiments, the nanoparticles are loaded with a therapeutically effective amount of at least one bioactive agent, wherein the bioactive agent is selected from a group consisting of proteins, peptides, nucleosides, nucleotides, antiviral agents, antineoplastic agents, antibiotics, and anti-inflammatory drugs. Further, the bioactive agent may be selected from a group consisting of calcitonin, cyclosporin, insulin, oxytocin, tyrosine, enkephalin, tyrotropin releasing hormone, follicle stimulating hormone, luteinizing hormone, vasopressin and vasopressin analogs, catalase, superoxide dismutase, interleukin-II, interferon, colony stimulating factor, tumor necrosis factor and melanocyte-stimulating hormone. In one preferred embodiment, the bioactive agent is an Alzheimer antagonist.

Some aspects of the invention relate to an oral dose of nanoparticles that effectively enhance intestinal or blood brain paracellular transport comprising γ-PGA and low molecular weight chitosan, wherein the chitosan dominates on a surface of the nanoparticles. Some aspects of the invention relate to an oral dose of nanoparticles that effectively enhance intestinal or blood brain paracellular transport comprising a negative component, such as γ-PGA or heparin, in the core and low molecular weight chitosan, wherein the chitosan dominates on a surface of the nanoparticles with positive charges. In a further embodiment, the nanoparticles comprise at least one bioactive agent, such as insulin, insulin analog, Alzheimer's disease antagonist, Parkison's disease antagonist, or other protein/peptide. The bioactive agent for treating Alzheimer's disease may include memantine hydrochloride (Axura® by Merz Pharmaceuticals), donepezil hydrochloride (Aricept® by Eisai Co. Ltd.), rivastigmine tartrate (Exelon® by Novartis), galantamine hydrochloride (Reminyl® by Johnson & Johnson), and tacrine hydrochloride (Cognex® by Parke Davis). Examples of insulin or insulin analog products include, but not limited to, Humulin® (by Eli Lilly), Humalog® (by Eli Lilly) and Lantus® (by Aventis).

Some aspects of the invention relate to an oral dose of nanoparticles that effectively enhance intestinal or blood brain paracellular transport comprising γ-PGA and low molecular weight chitosan, wherein the nanoparticles are crosslinked with a crosslinking agent or with light, such as ultraviolet irradiation.

Some aspects of the invention provide a dose of nanoparticles characterized by enhancing intestinal or brain blood paracellular transport, each nanoparticle comprising a first component of at least one bioactive agent, a second component of low molecular weight chitosan, and a third component that is negatively charged, wherein the second component dominates on a surface of the nanoparticle. In one embodiment, the third component is γ-PGA, heparin or alginate. In another embodiment, the first component comprises insulin at a concentration range of 0.075 to 0.091 mg/ml, the second component at a concentration range of 0.67 to 0.83 mg/ml, and the third component comprises γ-PGA at a concentration range of 0.150 to 0.184 mg/ml.

Some aspects of the invention provide a dose of nanoparticles characterized by enhancing intestinal or brain blood paracellular transport, each nanoparticle comprising a first component of at least one bioactive agent, a second component of low molecular weight chitosan, and a third component that is negatively charged, wherein the second component dominates on a surface of the nanoparticle, wherein the at least one bioactive agent is an antagonist for Alzheimer's disease or is for treating Alzheimer's disease selected from the group consisting of memantine hydrochloride, donepezil hydrochloride, rivastigmine tartrate, galantamine hydrochloride, and tacrine hydrochloride. In a further embodiment, the at least one bioactive agent is insulin or insulin analog. In still another embodiment, the at least one bioactive agent is selected from the group consisting of proteins, peptides, nucleosides, nucleotides, antiviral agents, antineoplastic agents, antibiotics, and anti-inflammatory drugs.

Some aspects of the invention provide a dose of nanoparticles characterized by enhancing intestinal or brain blood paracellular transport, wherein the nanoparticles are further encapsulated in a gelcap.

Some aspects of the invention provide a dose of nanoparticles characterized by enhancing intestinal or brain blood paracellular transport, each nanoparticle comprising a first component of at least one bioactive agent, a second component of low molecular weight chitosan, and a third component that is negatively charged, wherein the second component dominates on a surface of the nanoparticle, wherein the second component is crosslinked. In one embodiment, the degree of crosslinking is less than 50%. In another embodiment, the degree of crosslinking is ranged between 1% and 20%.

Some aspects of the invention provide a dose of nanoparticles characterized by enhancing intestinal or brain blood paracellular transport, each nanoparticle comprising a first component of at least one bioactive agent, a second component of low molecular weight chitosan, and a third component that is negatively charged, wherein the second component dominates on a surface of the nanoparticle, wherein the second component is crosslinked with a crosslinking agent selected from the group consisting of genipin, its derivatives, analog, stereoisomers and mixtures thereof In one embodiment, the crosslinking agent is selected from the group consisting of epoxy compounds, dialdehyde starch, glutaraldehyde, formaldehyde, dimethyl suberimidate, carbodiimides, succinimidyls, diisocyanates, acyl azide, reuterin, ultraviolet irradiation, dehydrothermal treatment, tris(hydroxymethyl) phosphine, ascorbate-copper, glucose-lysine and photo-oxidizers.

Some aspects of the invention provide a dose of nanoparticles characterized by enhancing intestinal or brain blood paracellular transport, wherein the low molecule weight chitosan has a molecular weight of 80 kDa or less.

Some aspects of the invention provide a method of enhancing intestinal or blood brain paracellular transport comprising administering a dose of nanoparticles, wherein each nanoparticle comprises a first component of at least one bioactive agent, a second component of low molecular weight chitosan, and a third component that is negatively charged, wherein the second component dominates on a surface of the nanoparticle. In one embodiment, the step of administering the dose of nanoparticles is via oral administration for enhancing intestinal paracellular transport. In another embodiment, the step of administering the dose of nanoparticles is via venous administration or injection for enhancing brain blood paracellular transport.

BRIEF DESCRIPTION OF THE DRAWINGS

Additional objects and features of the present invention will become more apparent and the disclosure itself will be best understood from the following Detailed Description of the Exemplary Embodiments, when read with reference to the accompanying drawings.

DETAILED DESCRIPTION OF THE EXEMPLARY EMBODIMENTS

Figure 1:
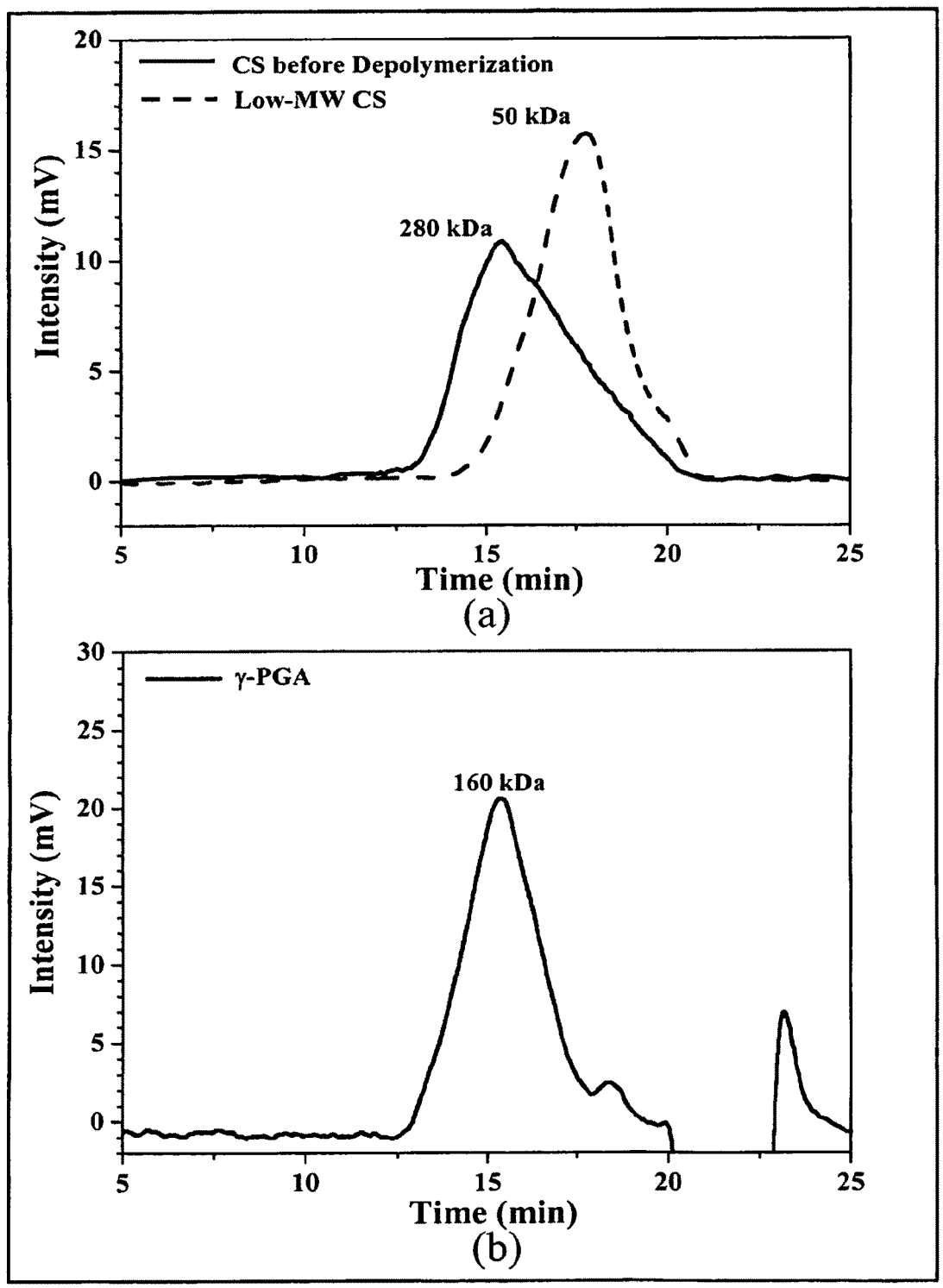
FIG. 1 shows GPC chromatograms of (a) standard-MW CS before depolymerization and the low-MW CS after depolymerization; (b) the purified γ-PGA obtained from microbial fermentation.

The preferred embodiments of the present invention described below relate particularly to preparation of nanoparticles composed of chitosan/poly-γ-glutamic acid/insulin and their permeability to enhance the intestinal or blood brain paracellular permeation by opening the tight junctions between epithelial cells. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

γ-PGA is a naturally occurring anionic homo-polyamide that is made of L-glutamic acid units connected by amide linkages between α-amino and γ-carboxylic acid groups (Crit. Rev. Biotechnol. 2001; 21:219-232). It is an exocellular polymer of certain *Bacillus* species that is produced within cells via the TCA cycle and is freely excreted into the fermentation broth. Its exact biological role is not fully known, although it is likely that γ-PGA is linked to increasing the survival of producing strains when exposed to environmental stresses. Because of its water-solubility, biodegradability, edibility, and non-toxicity toward humans and the environment, several applications of γ-PGA in food, cosmetics, medicine, and water treatment have been investigated in the past few years.

EXAMPLE No. 1

Materials and Methods of Nanoparticles Preparation

CS (MW ~2.8×10$^5$) with a degree of deacetylation of approximately 85% was acquired from Challenge Bioproducts Co. (Taichung, Taiwan). Acetic acid, cellulase (1.92 units/mg), fluorescein isothiocyanate (FITC), phosphate buffered saline (PBS), periodic acid, sodium acetate, formaldehyde, bismuth subnitrate, and Hanks balanced salt solution (HBSS) were purchased from Sigma Chemical Co. (St. Louis, Mo.). Ethanol absolute anhydrous and potassium sodium tartrate were obtained from Merck (Darmstadt, Germany). Non-essential amino acid (NEAA) solution, fetal bovine serum (FBS), gentamicin and trypsin-EDTA were acquired from Gibco (Grand Island, N.Y.). Eagle's minimal essential medium (MEM) was purchased from Bio West (Nuaille, France). All other chemicals and reagents used were of analytical grade.

EXAMPLE No. 2

Depolymerization of CS by Enzymatic Hydrolysis

Regular CS was treated with enzyme (cellulase) to produce low-MW CS according to a method described by Qin et al. with some modifications (Food Chem. 2004; 84:107-115). A solution of CS (20 g/l) was prepared by dissolving CS in 2% acetic acid. Care was taken to ensure total solubility of CS. Then, the CS solution was introduced into a vessel and adjusted to the desired pH 5.0 with 2N aqueous NaOH. Subsequently, cellulase (0.1 g) was added into the CS solution (100 ml) and continuously stirred at 37° C. for 12 hours. Afterward, the depolymerized CS was precipitated with aqueous NaOH at pH 7.0-7.2 and the precipitated CS was washed three times with deionized water. The resulting low-MW CS was lyophilized in a freeze dryer (Eyela Co. Ltd, Tokyo, Japan).

The average molecular weight of the depolymerized CS was determined by a gel permeation chromatography (GPC) system equipped with a series of PL aquagel-OH columns (one Guard 8 μm, 50×7.5 mm and two MIXED 8 μm, 300×7.5 mm, PL Laboratories, UK) and a refractive index (RI) detector (RI2000-F, SFD, Torrance, Calif.). Polysaccharide standards (molecular weights range from 180 to 788,000, Polymer Laboratories, UK) were used to construct a calibration curve. The mobile phase contained 0.01M $NaH_2PO_4$ and 0.5M $NaNO_3$ and was brought to a pH of 2.0. The flow rate of mobile phase was 1.0 ml/min, and the columns and the RI detector cell were maintained at 30° C.

Factors limiting applications of most commercially available CSs are their high molecular weight and thus high viscosity and poor solubility at physiological pH ranges. Low-MW CS overcomes these limitations and hence finds much wider applications in diversified fields. It was suggested that low-MW CS be used as a parenteral drug carrier due to its lower antigen effect (Eur. J. Pharm. Biopharm. 2004; 57:101-105). Low-MW CS was used as a non-viral gene delivery system and showed promising results (Int. J. Pharm. 1999; 178:231-243). Other studies based on animal testing showed the possibilities of low-MW CS for treatment of type 2 diabetes and gastric ulcer (Biol. Pharm. Bull. 2002; 25:188-192). Several hydrolytic enzymes such as lysozyme, pectinase, cellulase, bromelain, hemicellulase, lipase, papain and the like can be used to depolymerize CS (Biochim. Biophys. Acta 1996; 1291:5-15; Biochem. Eng. J. 2001; 7:85-88; Carbohydr. Res. 1992; 237:325-332). FIG. 1a shows GPC chromatograms of both standard-MW (also known as regular-MW) and low-MW CS. It is known that cellulase catalyzes the cleavage of the glycosidic linkage in CS (Food Chem. 2004; 84:107-115). The low-MW CS used in the study was obtained by precipitating the depolymerized CS solution with aqueous NaOH at pH 7.0-7.2. Thus obtained low-MW CS had a MW of about 50 kDa (FIG. 1a). In a preferred embodiment, the low molecular weight chitosan has a molecular weight of less than about 40 kDa.

It was observed that the obtained low-MW CS can be readily dissolved in an aqueous solution at pH 6.0, while that before depolymerization needs to be dissolved in an acetic acid solution with a pH value about 4.0. Additionally, it was found that with the low-MW CS, the prepared nanoparticles had a significantly smaller size with a narrower distribution than their counterparts prepared with the high-MW (also known as standard-MW) CS (before depolymerization), due to its lower viscosity. As an example, upon adding a 0.10% γ-PGA aqueous solution into a 0.20% high-MW CS solution (viscosity 5.73±0.08 cp, measured by a viscometer), the mean particle size of the prepared nanoparticles was 878.3±28.4 nm with a polydispersity index of 1.0, whereas adding a 0.10% γ-PGA aqueous solution into the low-MW CS solution (viscosity 1.29±0.02 cp) formed nanoparticles with a mean particle size of 218.1±4.1 nm with a polydispersity index of 0.3 (n=5).

EXAMPLE No. 3

Production and Purification of γ-PGA

γ-PGA was produced by *Bacillus licheniformis* (ATCC 9945, Bioresources Collection and Research Center, Hsinchu, Taiwan) as per a method reported by Yoon et al. with slight modifications (Biotechnol. Lett. 2000; 22:585-588). Highly mucoid colonies (ATCC 9945a) were selected from *Bacillus licheniformis* (ATCC 9945) cultured on the E medium (ingredients comprising L-glutamic acid, 20.0 g/l; citric acid, 12.0 g/l; glycerol, 80.0 g/l; $NH_4Cl$, 7.0 g/l; $K_2HPO_4$, 0.5 g/l; $MgSO_4.7H_2O$, 0.5 g/l; $FeCl_3.6H_2O$, 0.04 g/l; $CaCl_2.2H_2O$, 0.15 g/l; $MnSO_4.H_2O$, 0.104 g/l, pH 6.5) agar plates at 37° C. for several times. Subsequently young mucoid colonies were transferred into 10 ml E medium and grown at 37° C. in a shaking incubator at 250 rpm for 24 hours. Afterward, 500 μl of culture broth was mixed with 50 ml E medium and was transferred into a 2.5-l jar-fermentor (KMJ-2B, Mituwa Co., Osaka, Japan) containing 950 ml of E medium. Cells were cultured at 37° C. The pH was controlled at 6.5 by automatic feeding of 25% (v/v) $NH_4OH$ and/or 2M HCl. The dissolved oxygen concentration was initially controlled at 40% of air saturation by supplying air and by controlling the agitation speed up to 1000 rpm.

After 40 hours, cells were separated from the culture broth by centrifugation for 20 minutes at 12,000×g at 4° C. The supernatant containing γ-PGA was poured into 4 volumes of methanol and left overnight with gentle stirring. The resulting precipitate containing crude γ-PGA was collected by centrifugation for 40 minutes at 12,000×g at 4° C. and then was dissolved in deionized water to remove insoluble impurities by centrifugation for 20 minutes at 24,000×g at 4° C. The aqueous γ-PGA solution was desalted by dialysis (MWCO: 100,000, Spectrum Laboratories, Inc., Laguna Hills, Calif.) against distilled water for 12 hours with water exchanges several times, and finally was lyophilized to obtain pure γ-PGA.

The purified γ-PGA was verified by the proton nuclear magnetic resonance ($^1$H-NMR) and the FT-IR analyses. Analysis of $^1$H-NMR was conducted on an NMR spectrometer (Varian Unityionva 500 NMR Spectrometer, MO) using DMSO-$d_6$ at 2.49 ppm as an internal reference. Test samples used for the FT-IR analysis first were dried and ground into a powder form. The powder then was mixed with KBr (1:100) and pressed into a disk. Analysis was performed on an FT-IR spectrometer (Perkin Elmer Spectrum RX1 FT-IR System, Buckinghamshire, England). The samples were scanned from 400-4000 $cm^{-1}$. The average molecular weight of the purified γ-PGA was determined by the same GPC system as described before. Polyethylene glycol (molecular weights of 106-22, 000) and polyethylene oxide (molecular weights of 20,000-1,000,000, PL Laboratories) standards were used to construct a calibration curve. The mobile phase contained 0.01M $NaH_2PO_4$ and 0.2M $NaNO_3$ and was brought to a pH of 7.0.

Figure 2:
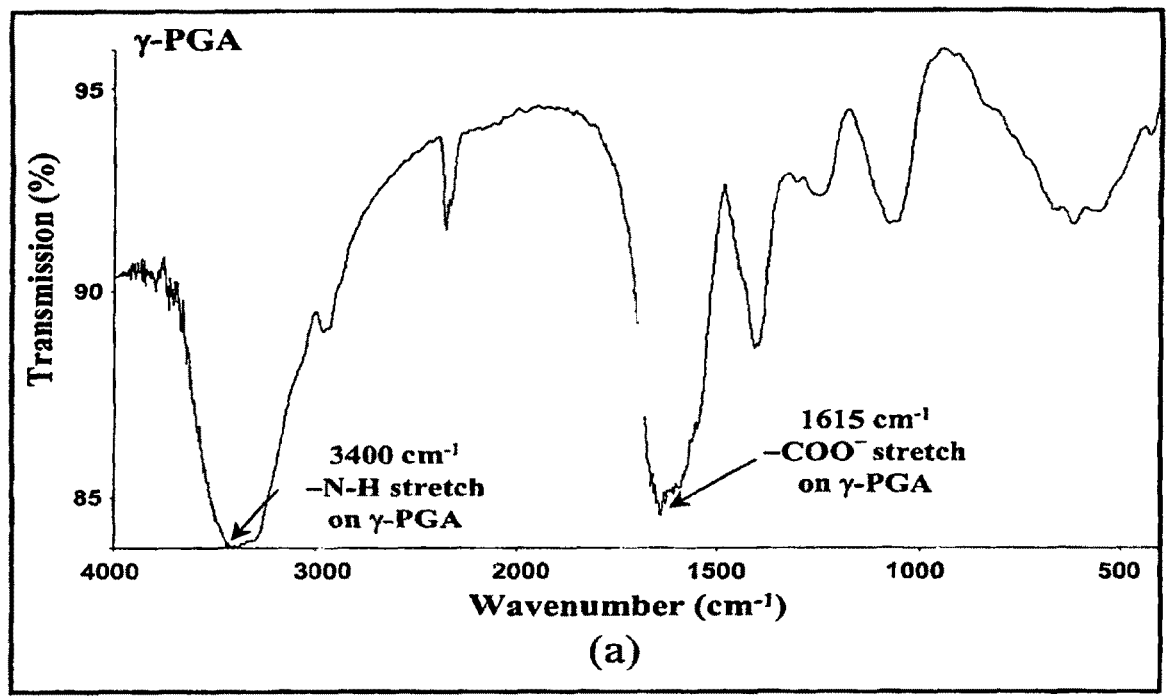
FIG. 2 shows (a) FT-IR and (b) $^1$H-NMR spectra of the purified γ-PGA obtained from microbial fermentation.
Figure 2:
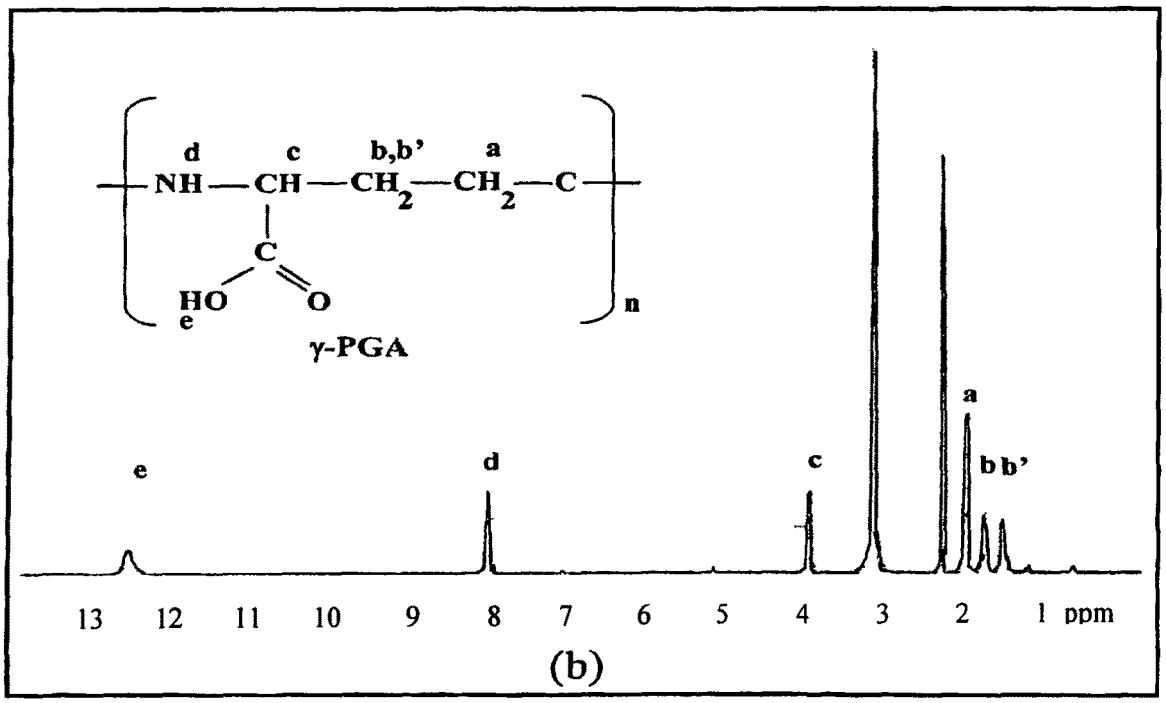

The purified γ-PGA obtained from fermentation was analyzed by GPC, $^1$H-NMR, and FT-IR. As analyzed by GPC (FIG. 1b), the purified γ-PGA had a MW of about 160 kDa. In the FT-IR spectrum (FIG. 2a), a characteristic peak at 1615 $cm^{-1}$ for the associated carboxylic acid salt (—$COO^-$ antisymmetric stretch) on γ-PGA was observed. The characteristic absorption due to C=O in secondary amides (amide I band) was overlapped by the characteristic peak of —COO⁻. Additionally, the characteristic peak observed at 3400 cm$^{-1}$ was the N—H stretch of γ-PGA. In the $^1$H-NMR spectrum (FIG. 2b), six chief signals were observed at 1.73 and 1.94 ppm (β-CH$_2$), 2.19 ppm (γ-CH$_2$), 4.14 ppm (α-CH), 8.15 ppm (amide), and 12.58 ppm (COOH). These results indicated that the observed FT-IR and $^1$H-NMR spectra correspond well to those expected for γ-PGA. Additionally, the fermented product after purification showed no detected macromolecular impurities by the $^1$H-NMR analysis, suggesting that the obtained white power of γ-PGA is highly pure.

EXAMPLE No. 4

Preparation of the CS-γ-PGA Nanoparticles

Nanoparticles were obtained upon addition of γ-PGA aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) at varying concentrations (0.01%, 0.05%, 0.10%, 0.15%, or 0.20% by w/v) under magnetic stirring at room temperature. Nanoparticles were collected by ultracentrifugation at 38,000 rpm for 1 hour. Supernatants were discarded and nanoparticles were resuspended in deionized water for further studies. FT-IR was used to analyze peak variations of amino groups of low-MW CS and carboxylic acid salts of γ-PGA in the CS-γ-PGA nanoparticles.

Figure 3:
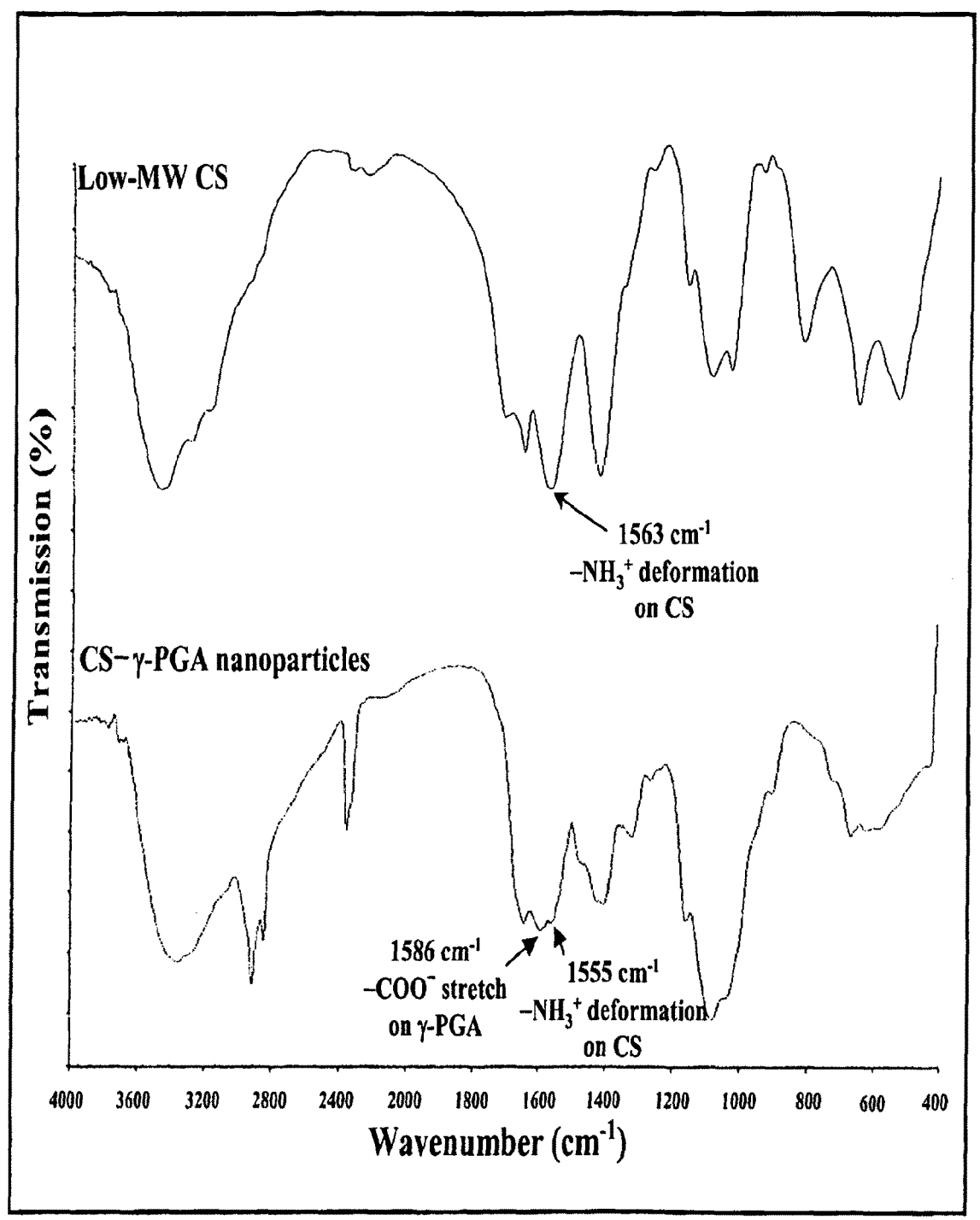
FIG. 3 shows FT-IR spectra of the low-MW CS and the prepared CS-γ-PGA nanoparticles.

As stated, nanoparticles were obtained instantaneously upon addition of a γ-PGA aqueous solution (pH 7.4) into a low-MW CS aqueous solution (pH 6.0) under magnetic stirring at room temperature. FIG. 3 shows the FT-IR spectra of the low-MW CS and the CS-γ-PGA nanoparticles. As shown in the spectrum of CS, the characteristic peak observed at 1563 cm$^{-1}$ was the protonated amino group (—NH$_3^+$ deformation) on CS. In the spectrum of CS-γ-PGA complex, the characteristic peak at 1615 cm$^{-1}$ for —COO⁻ on γ-PGA disappeared and a new peak at 1586 cm$^{-1}$ appeared, while the characteristic peak of —NH$_3^+$ deformation on CS at 1563 cm$^{-1}$ shifted to 1555 cm$^{-1}$. These observations are attributed to the electrostatic interaction between the negatively charged carboxylic acid salts (—COO⁻) on γ-PGA and the positively charged amino groups (—NH$_3^+$) on CS (Int. J. Pharm. 2003; 250:215-226). The electrostatic interaction between the two polyelectrolytes (γ-PGA and CS) instantaneously induced the formation of long hydrophobic segments (or at least segments with a high density of neutral ion-pairs), and thus resulted in highly neutralized complexes that segregated into colloidal nanoparticles (Langmuir. 2004; 20:7766-7778).

EXAMPLE No. 5

Characterization of the CS-γ-PGA Nanoparticles

The morphological examination of the CS-γ-PGA nanoparticles was performed by TEM (transmission electron microscopy) and AFM (atomic force microscopy). The TEM sample was prepared by placing a drop of the nanoparticle solution onto a 400 mesh copper grid coated with carbon. About 2 minutes after deposition, the grid was tapped with a filter paper to remove surface water and positively stained by using an alkaline bismuth solution (Microbiol. Immunol. 1986; 30:1207-1211). The AFM sample was prepared by casting a drop of the nanoparticle solution on a slide glass and then dried in vacuum. The size distribution and zeta potential of the prepared nanoparticles were measured using a Zetasizer (3000HS, Malvern Instruments Ltd., Worcestershire, UK).

During storage, aggregation of nanoparticles may occur and thus leads to losing their structural integrity or forming precipitation of nanoparticles (Eur. J. Pharm. Sci. 1999; 8:99-107). Therefore, the stability of nanoparticles during storage must be evaluated. In the stability study, the prepared nanoparticles suspended in deionized water (1 mg/ml) were stored at 4° C. and their particle sizes and zeta potential values were monitored by the same Zetasizer as mentioned earlier during storage.

In the preparation of nanoparticles, samples were visually analyzed and three distinct solution systems were identified: clear solution, opalescent suspension, and solution with precipitation of aggregates. Examined by the Zetasizer, nanoparticles were found in the clear solution and the opalescent suspension rather than in the solution with precipitation of aggregates.

Figure 4:
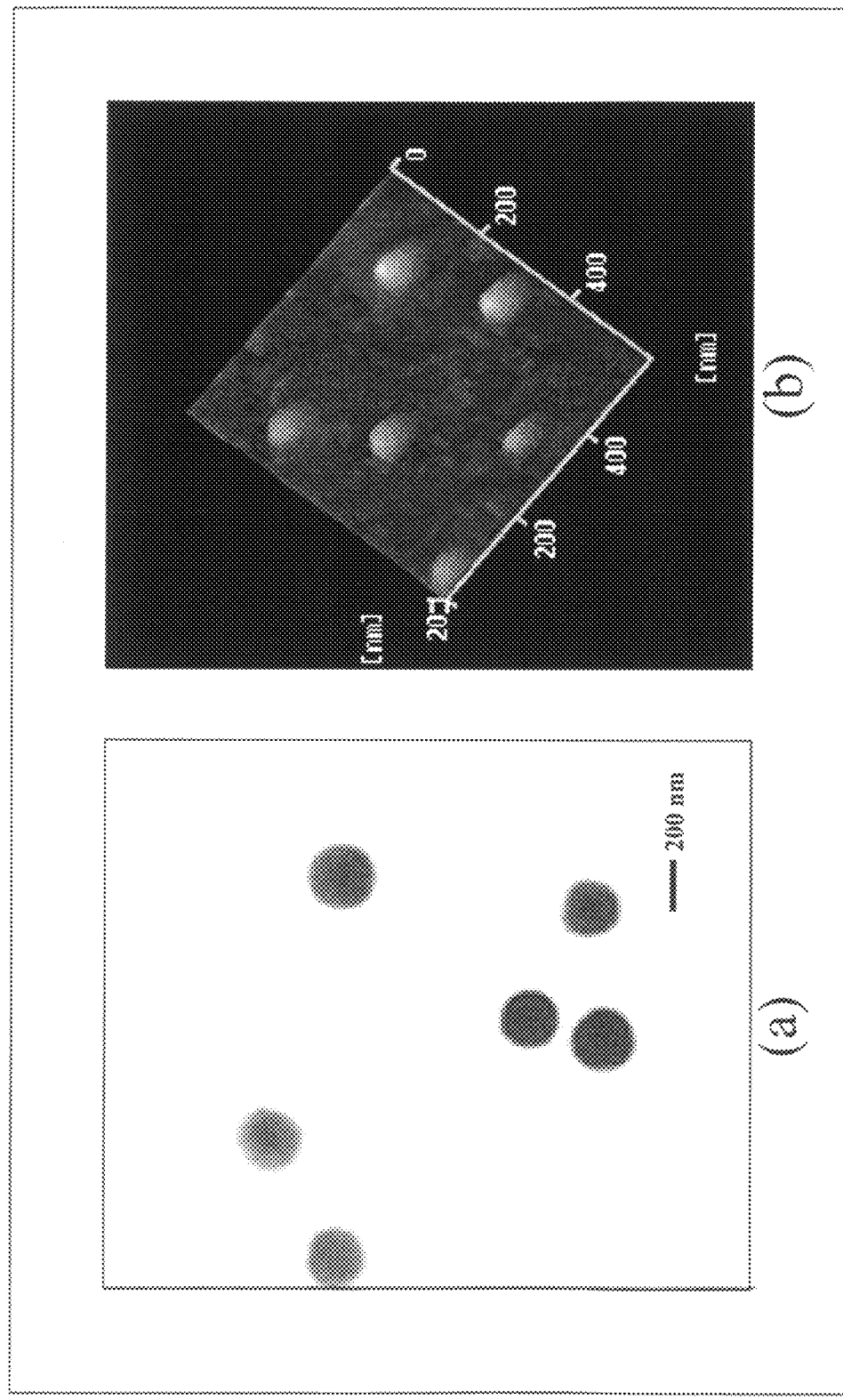
FIG. 4 shows (a) a TEM micrograph of the prepared CS-γ-PGA nanoparticles (0.10% γ-PGA:0.20% CS) and (b) an AFM micrograph of the prepared CS-γ-PGA nanoparticles (0.01% γ-PGA:0.01% CS).

The particle sizes and the zeta potential values of CS-γ-PGA nanoparticles, prepared at varying concentrations of γ-PGA and CS, were determined and the results are shown in Tables 1a and 1b. It was found that the particle size and the zeta potential value of the prepared nanoparticles were mainly determined by the relative amount of the local concentration of γ-PGA in the added solution to the surrounding concentration of CS in the sink solution. At a fixed concentration of CS, an increase in the γ-PGA concentration allowed γ-PGA molecules interacting with more CS molecules, and thus formed a lager size of nanoparticles (Table 1a, p<0.05). When the amount of CS molecules exceeded that of local γ-PGA molecules, some of the excessive CS molecules were entangled onto the surfaces of CS-γ-PGA nanoparticles. Thus, the resulting nanoparticles may display a structure of a neutral polyelectrolyte-complex core surrounded by a positively charged CS shell (Table 1b) ensuring the colloidal stabilization (Langmuir. 2004; 20:7766-7778). In contrast, as the amount of local γ-PGA molecules sufficiently exceeded that of surrounding CS molecules, the formed nanoparticles had γ-PGA exposed on the surfaces and thus had a negative charge of zeta potential. Therefore, the particle size and the zeta potential value of the prepared CS-γ-PGA nanoparticles can be controlled by their constituted compositions. The results obtained by the TEM and AFM examinations showed that the morphology of the prepared nanoparticles was spherical in shape with a smooth surface (FIGS. 4a and 4b). Some aspects of the invention relate to nanoparticles having a mean particle size between about 50 and 400 nanometers, preferably between about 100 and 300 nanometers, and most preferably between about 100 and 200 nanometers. The morphology of the nanoparticles shows spherical in shape with a smooth surface at any pH between 2.5 and 6.6. In one embodiment, the stability of the nanoparticles of the present invention at a low pH around 2.5 enables the nanoparticles to be intact when exposed to the acidic medium in the stomach.

Figure 5:
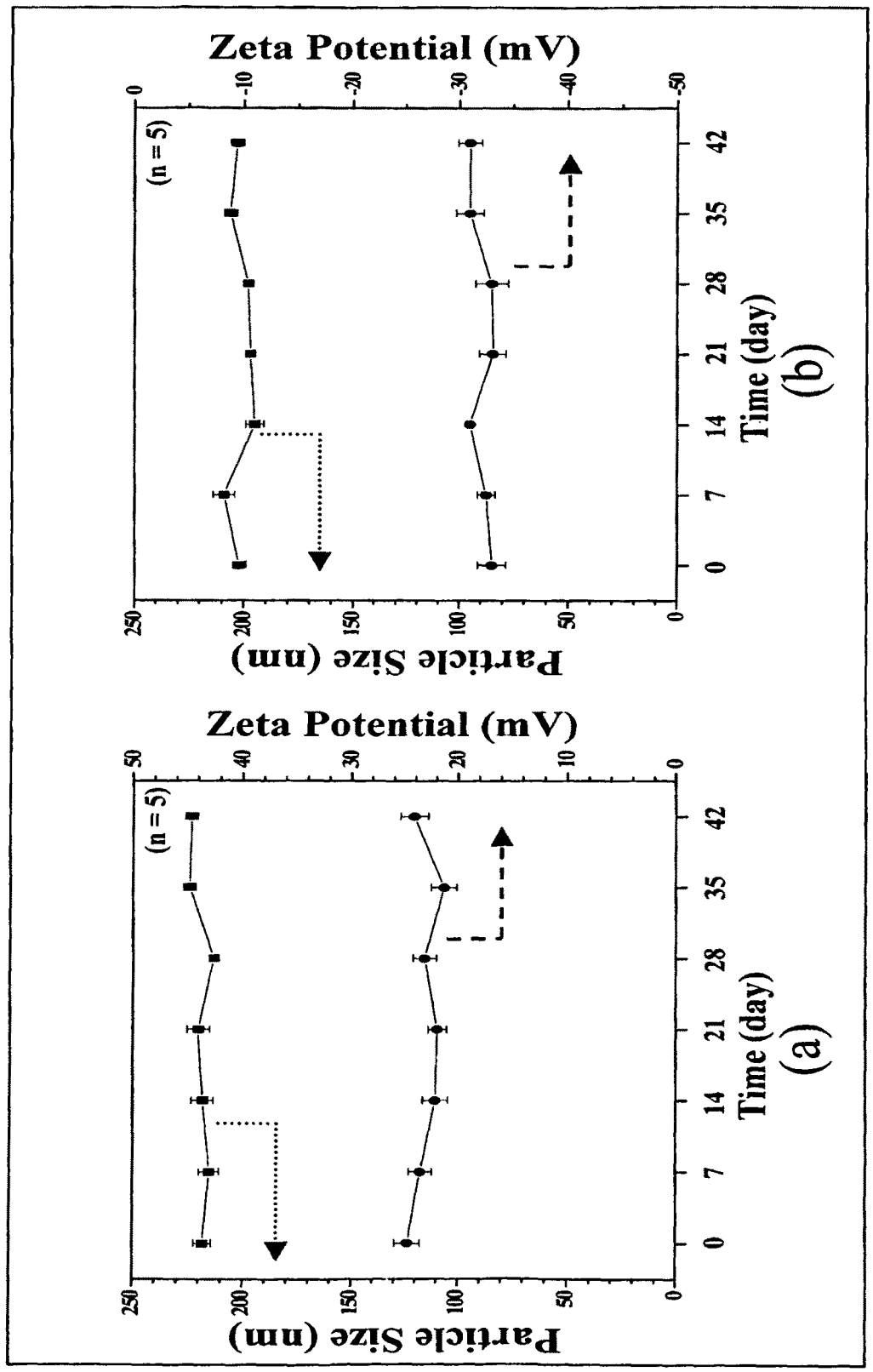
FIG. 5 shows changes in particle size and zeta potential of (a) the CS-γ-PGA nanoparticles (0.10% γ-PGA:0.20% CS) and (b) the CS-γ-PGA nanoparticles (0.10% γ-PGA:0.01% CS) during storage for up to 6 weeks.

Two representative groups of the prepared nanoparticles were selected for the stability study: one with a positive surface charge (0.10% γ-PGA:0.20% CS) and the other with a negative surface charge (0.10% γ-PGA:0.01% CS). FIG. 5 shows changes in particle size (■, mean diameter) and zeta potential (●) of (a) the CS-γ-PGA nanoparticles (0.10% γ-PGA:0.20% CS) and (b) the CS-γ-PGA nanoparticles (0.10% γ-PGA:0.01% CS) during storage for up to 6 weeks. It was found that neither aggregation nor precipitation of nanoparticles was observed during storage for up to 6 weeks, as a result of the electrostatic repulsion between the positively charged CS-γ-PGA nanoparticles (for the former group) or the negatively charged CS-γ-PGA nanoparticles (for the latter group). Additionally, changes in particle size and zeta potential of the nanoparticles were minimal for both studied groups (FIGS. 5*a* and 5*b*). These results demonstrated that the prepared nanoparticles suspended in deionized water were stable during storage.

EXAMPLE No. 6

Caco-2 Cell Cultures and TEER Measurements

Caco-2 cells were seeded on the tissue-culture-treated polycarbonate filters (diameter 24.5 mm, growth area 4.7 cm$^2$) in Costar Transwell 6 wells/plates (Corning Costar Corp., NY) at a seeding density of $3\times10^5$ cells/insert. MEM (pH 7.4) supplemented with TABLE 1a Effects of concentrations of γ-PGA and CS on the particle sizes of the prepared CS-γ-PGA nanoparticles
Mean Particle Size (nm, n = 5)

| γ-PGA | CS | | | | |
|---|---|---|---|---|---|
| | 0.01%[a] | 0.05% | 0.10% | 0.15% | 0.20% |
| 0.01%[b] | 79.0 ± 3.0 | 103.1 ± 4.6 | 96.7 ± 1.9 | 103.6 ± 1.9 | 140.5 ± 2.0 |
| 0.05% | 157.4 ± 1.7 | 120.8 ± 3.9 | 144.5 ± 2.4 | 106.2 ± 3.8 | 165.4 ± 1.7 |
| 0.10% | 202.2 ± 3.1 | 232.6 ± 1.2 | 161.0 ± 1.8 | 143.7 ± 2.7 | 218.1 ± 4.1 |
| 0.15% | 277.7 ± 3.2 | 264.9 ± 2.1 | 188.6 ± 2.9 | 178.0 ± 2.2 | 301.1 ± 6.4 |
| 0.20% | 284.1 ± 2.1 | 402.2 ± 4.0 | ▲ | 225.5 ± 3.1 | 365.5 ± 5.1 |

[a] concentration of CS (by w/v)
[b] concentration of γ-PGA (by w/v)
▲ precipitation of aggregates was observed TABLE 1b Effects of concentrations of γ-PGA and CS on the zeta potential values of the prepared CS-γ-PGA nanoparticles.
Zeta Potential (mV, n = 5)

| γ-PGA | CS | | | | |
|---|---|---|---|---|---|
| | 0.01%[a] | 0.05% | 0.10% | 0.15% | 0.20% |
| 0.01%[b] | 15.4 ± 0.3 | 22.8 ± 0.5 | 19.8 ± 1.5 | 16.5 ± 1.4 | 17.2 ± 1.6 |
| 0.05% | −32.7 ± 0.7 | 23.7 ± 1.7 | 27.6 ± 0.7 | 20.3 ± 0.8 | 19.2 ± 0.6 |
| 0.10% | −33.1 ± 1.3 | 21.1 ± 1.6 | 20.3 ± 1.1 | 23.6 ± 0.9 | 24.7 ± 1.2 |
| 0.15% | −33.2 ± 2.1 | −21.9 ± 2.0 | 19.2 ± 0.4 | 16.9 ± 1.7 | 19.8 ± 0.3 |
| 0.20% | −34.5 ± 0.5 | −34.6 ± 0.3 | ▲ | 14.6 ± 0.7 | 16.3 ± 0.7 |

[a] concentration of CS (by w/v)
[b] concentration of γ-PGA (by w/v)
▲ precipitation of aggregates was observed 20% FBS, 1% NEAA, and 40 μg/ml antibiotic-gentamicin was used as the culture medium, and added to both the donor and acceptor compartments. The medium was replaced every 48 hours for the first 6 days and every 24 hours thereafter. The cultures were kept in an atmosphere of 95% air and 5% $CO_2$ at 37° C. and were used for the paracellular transport experiments 18-21 days after seeding (TEER values in the range of 600-800 Ωcm$^2$).

TEER values of the Caco-2 cell monolayers were monitored with a Millicell®-Electrical Resistance System (Millipore Corp., Bedford, Mass.) connected to a pair of chopstick electrodes. To initiate the transport experiments, the culture media in the donor and acceptor compartments were aspirated, and the cells were rinsed twice with pre-warmed transport media (HBSS supplemented with 25 mM glucose, pH 6.0). Following a 30-min equilibration with the transport media at 37° C., the cells were incubated for 2 hours with 2 ml transport media containing 0.5 ml test nanoparticle solutions (0.2 mg/ml) at 37° C. Subsequently, solutions of nanoparticles were carefully removed and cells were washed three times with HBSS and replaced by fresh culture media. The TEER was measured for another 20 hours to study reversibility of the effect of test nanoparticles on Caco-2 cell monolayers (Eur. J. Pharm. Sci. 2000; 10:205-214).

The intercellular tight junction is one of the major barriers to the paracellular transport of macromolecules (J. Control. Release 1996; 39:131-138; J. Control. Release 1998; 51:35-46). Trans-epithelial ion transport is contemplated to be a good indication of the tightness of the junctions between cells and was evaluated by measuring TEER of Caco-2 cell monolayers in the study. It was reported that the measurement of TEER can be used to predict the paracellular transport of hydrophilic molecules (Eur. J. Pharm. Biopharm. 2004; 58:225-235). When the tight junctions open, the TEER value will be reduced due to the water and ion passage through the paracellular route. Caco-2 cell monolayers have been widely used as an in vitro model to evaluate the intestinal paracellular permeability of macromolecules.

Figure 6:
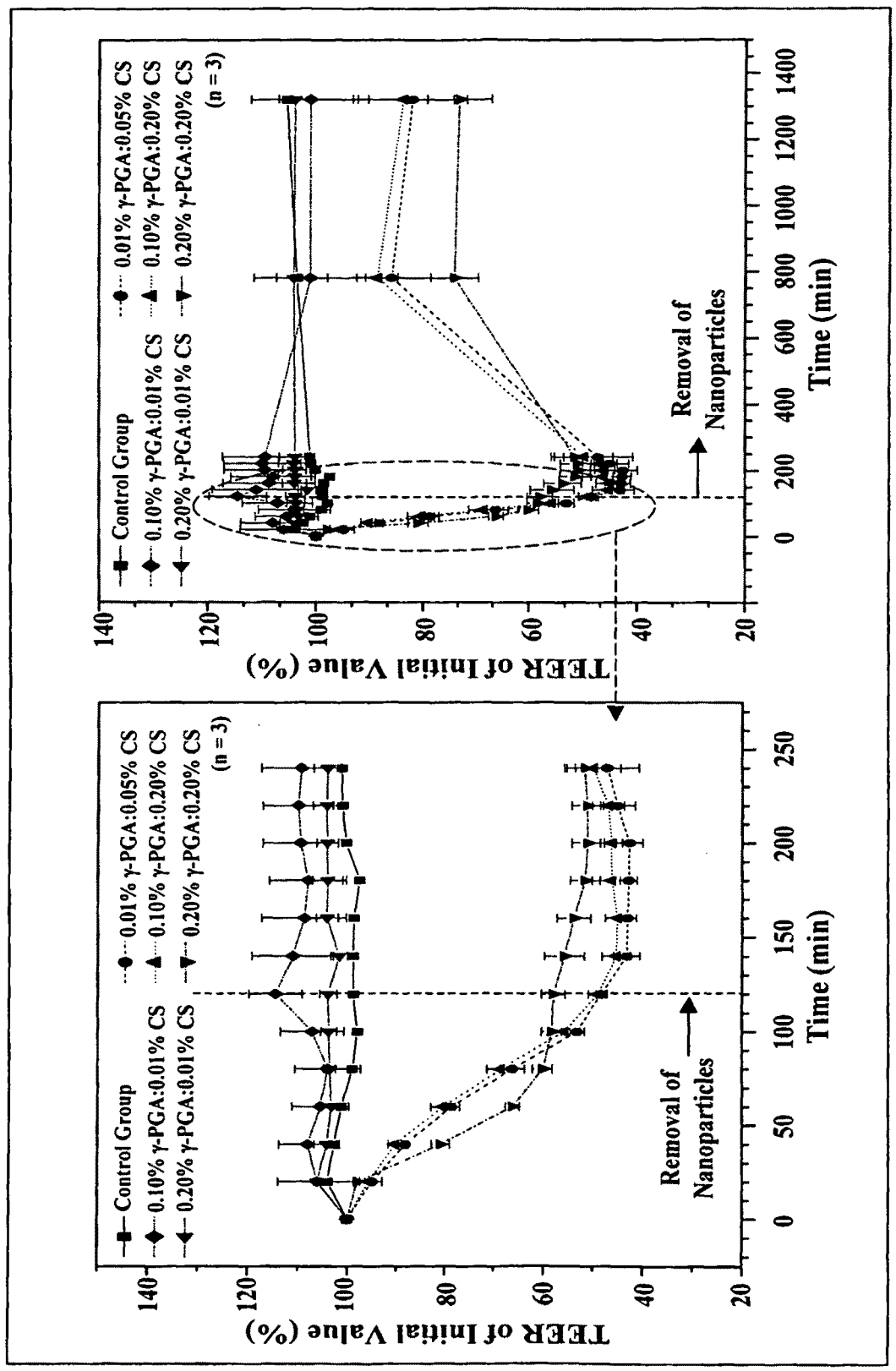
FIG. 6 shows effects of the prepared CS-γ-PGA nanoparticles on the TEER values of Caco-2 cell monolayers.

Effects of the prepared CS-γ-PGA nanoparticles on the TEER values of Caco-2 cell monolayers are shown in FIG. 6. As shown, the prepared nanoparticles with a positive surface charge (CS dominated on the surface, 0.01% γ-PGA:0.05% CS, 0.10% γ-PGA:0.2% CS, and 0.20% γ-PGA:0.20% CS) were able to reduce the values of TEER of Caco-2 cell monolayers significantly ($p<0.05$). After a 2-hour incubation with these nanoparticles, the TEER values of Caco-2 cell monolayers were reduced to about 50% of their initial values as compared to the control group (without addition of nanoparticles in the transport media). This indicated that the nanoparticles with CS dominated on the surfaces could effectively open the tight junctions between Caco-2 cells, resulting in a decrease in the TEER values. It was reported that interaction of the positively charged amino groups of CS with the negatively charged sites on cell surfaces and tight junctions induces a redistribution of F-actin and the tight junction's protein ZO-1, which accompanies the increased paracellular permeability (Drug Deliv. Rev. 2001; 50:S91-S101). It is suggested that an interaction between chitosan and the tight junction protein ZO-1, leads to its translocation to the cytoskeleton.

After removal of the incubated nanoparticles, a gradual increase in TEER values was noticed. This phenomenon indicated that the intercellular tight junctions of Caco-2 cell monolayers started to recover gradually; however, the TEER values did not recover to their initial values (FIG. 6). Kotzé et al. reported that complete removal of a CS-derived polymer, without damaging the cultured cells, was difficult due to the highly adhesive feature of CS (Pharm. Res. 1997; 14:1197-1202). This might be the reason why the TEER values did not recover to their initial values. In contrast, the TEER values of Caco-2 cell monolayers incubated with the nanoparticles with a negative surface charge (γ-PGA dominated on the surface, 0.10% γ-PGA:0.01% CS and 0.20% γ-PGA:0.01% CS, FIG. 6) showed no significant differences as compared to the control group (p>0.05). This indicated that γ-PGA does not have any effects on the opening of the intercellular tight junctions.

Figure 8:
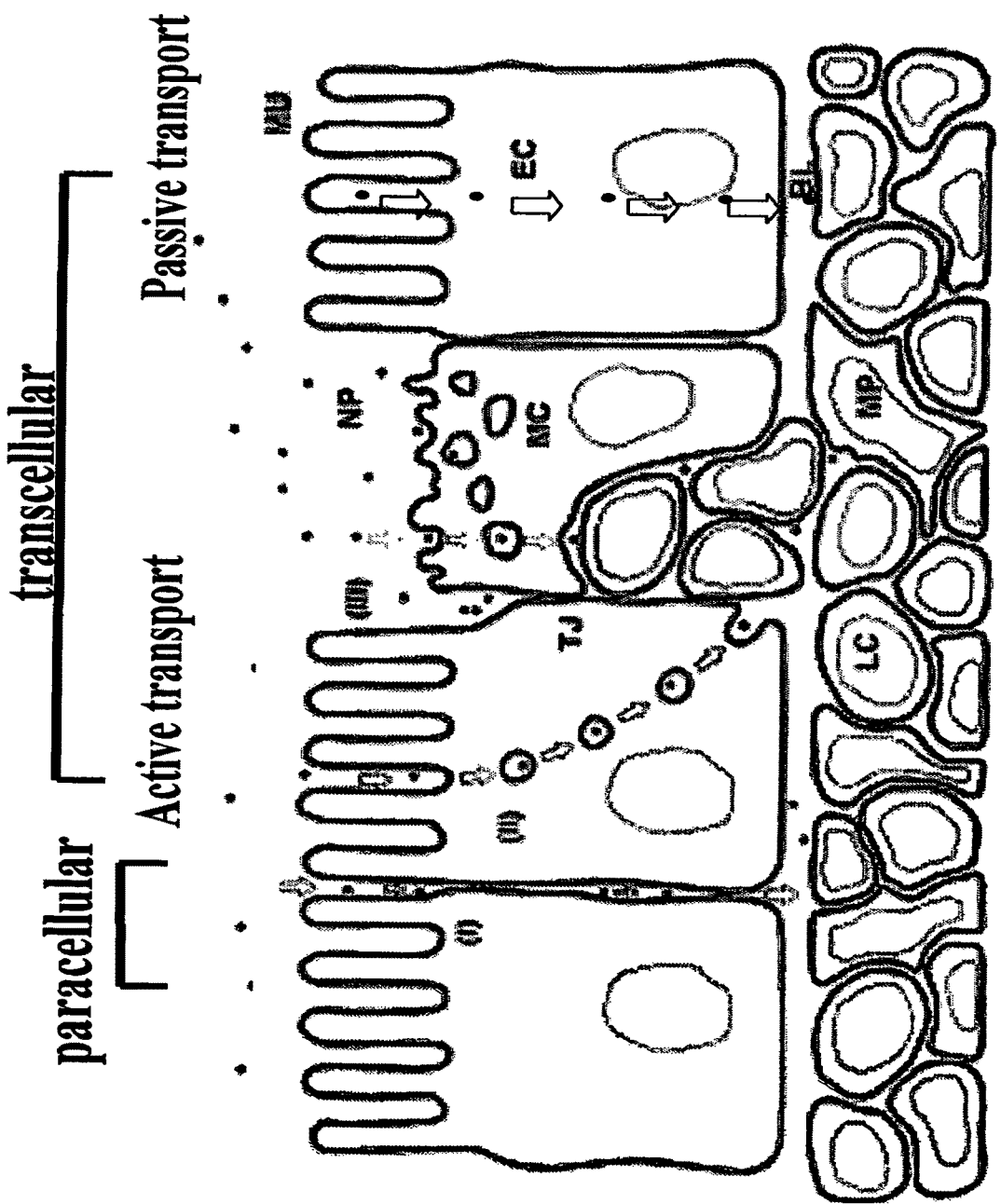
FIG. 8 shows an illustrative protein transport mechanism through a cell layer, including transcellular transport and paracelluler transport.
Figure 9:
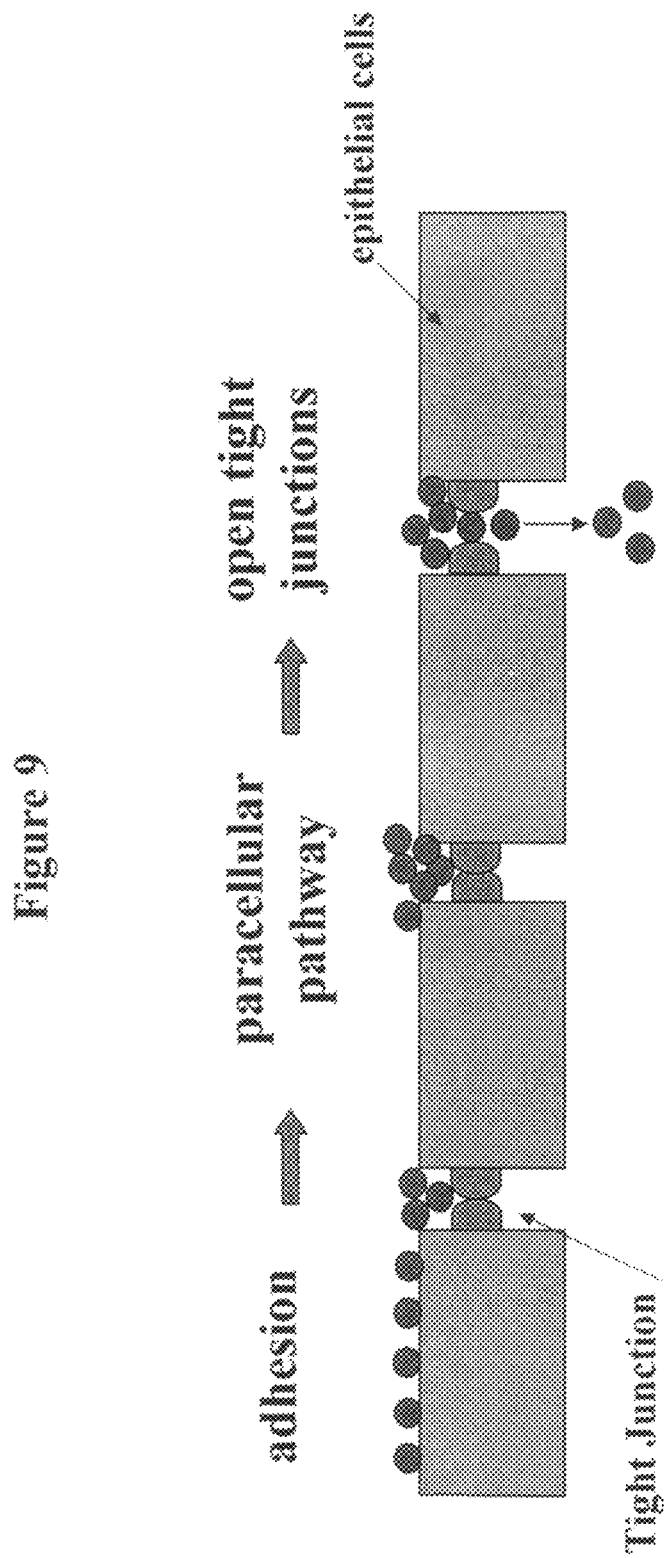
FIG. 9 shows a schematic illustration of a paracellular transport mechanism.

FIG. 8 shows an illustrative protein transport mechanism through a cellular layer, including transcellular transport and paracelluler transport. FIG. 9 shows a schematic illustration of a paracellular transport mechanism. The transcellular protein or peptide transport may be an active transport or a passive transport mode whereas the paracellular transport is basically a passive mode. Ward et al. reported and reviewed current knowledge regarding the physiological regulation of tight junctions and paracellular permeability (PSTT 2000; 3:346-358). Chitosan as nanoparticle vehicles for oral delivery of protein drugs avoids the enzymatic inactivation in the gastrointestinal conduit. The chitosan component of the present nanoparticles has a special feature of adhering to the mucosal surface and transiently opening the tight junctions between epithelial cells.

EXAMPLE No. 7 fCS-γ-PGA Nanoparticle Preparation and CLSM Visualization

Figure 10:
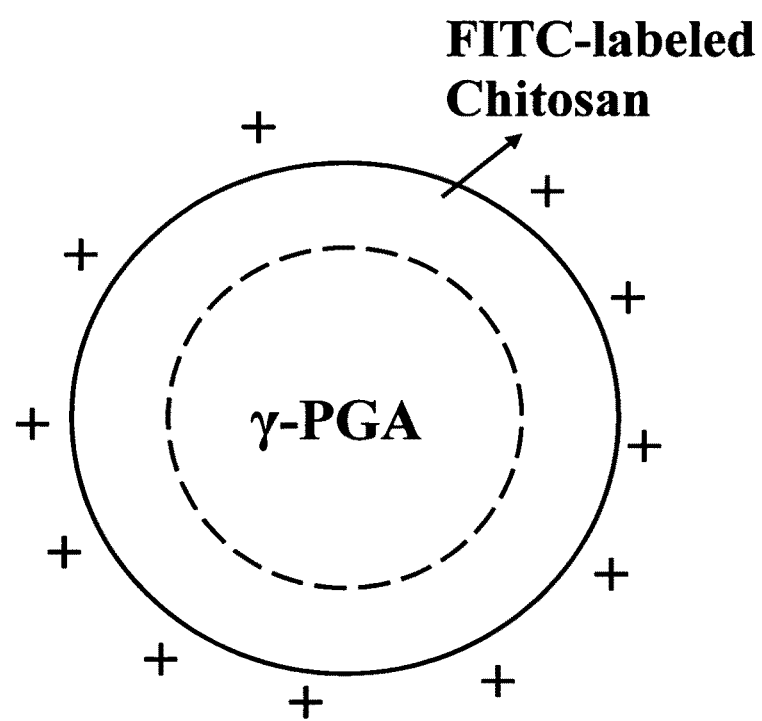
FIG. 10 shows an fCS-γ-PGA nanoparticle with FITC-labeled chitosans having positive surface charge.

Fluorescence (FITC)-labeled CS-γ-PGA (fCS-γ-PGA) nanoparticles (FIG. 10) were prepared for the confocal laser scanning microscopy (CLSM) study. The nanoparticles of the present invention display a structure of a neutral polyelectrolyte-complex core surrounded by a positively charged chitosan shell. Synthesis of the FITC-labeled low-MW CS (fCS) was based on the reaction between the isothiocyanate group of FITC and the primary amino groups of CS as reported in the literature (Pharm. Res. 2003; 20:1812-1819). Briefly, 100 mg of FITC in 150 ml of dehydrated methanol were added to 100 ml of 1% low-MW CS in 0.1M acetic acid. After 3 hours of reaction in the dark at ambient conditions, fCS was precipitated by raising the pH to about 8-9 with 0.5M NaOH. To remove the unconjugated FITC, the precipitate was subjected to repeated cycles of washing and centrifugation (40,000×g for 10 min) until no fluorescence was detected in the supernatant. The fCS dissolved in 80 ml of 0.1M acetic acid was then dialyzed for 3 days in the dark against 5 liters of distilled water, with water replaced on a daily basis. The resultant fCS was lyophilized in a freeze dryer. The fCS-γ-PGA nanoparticles were prepared as per the procedure described in Example No. 4.

Subsequently, the transport medium containing fCS-γ-PGA nanoparticles (0.2 mg/ml) was introduced into the donor compartment of Caco-2 cells, which were pre-cultured on the transwell for 18-21 days. The experimental temperature was maintained at 37° C. by a temperature control system (DH-35 Culture Dish Heater, Warner Instruments Inc., Hamden, Conn.). After incubation for specific time intervals, test samples were aspirated. The cells were then washed twice with pre-warmed PBS solution before they were fixed in 3.7% paraformaldehyde (Pharm. Res. 2003; 20:1812-1819). Cells were examined under an inversed CLSM (TCS SL, Leica, Germany). The fluorescence images were observed using an argon laser (excitation at 488 nm, emission collected at a range of 510-540 nm).

Figure 7:
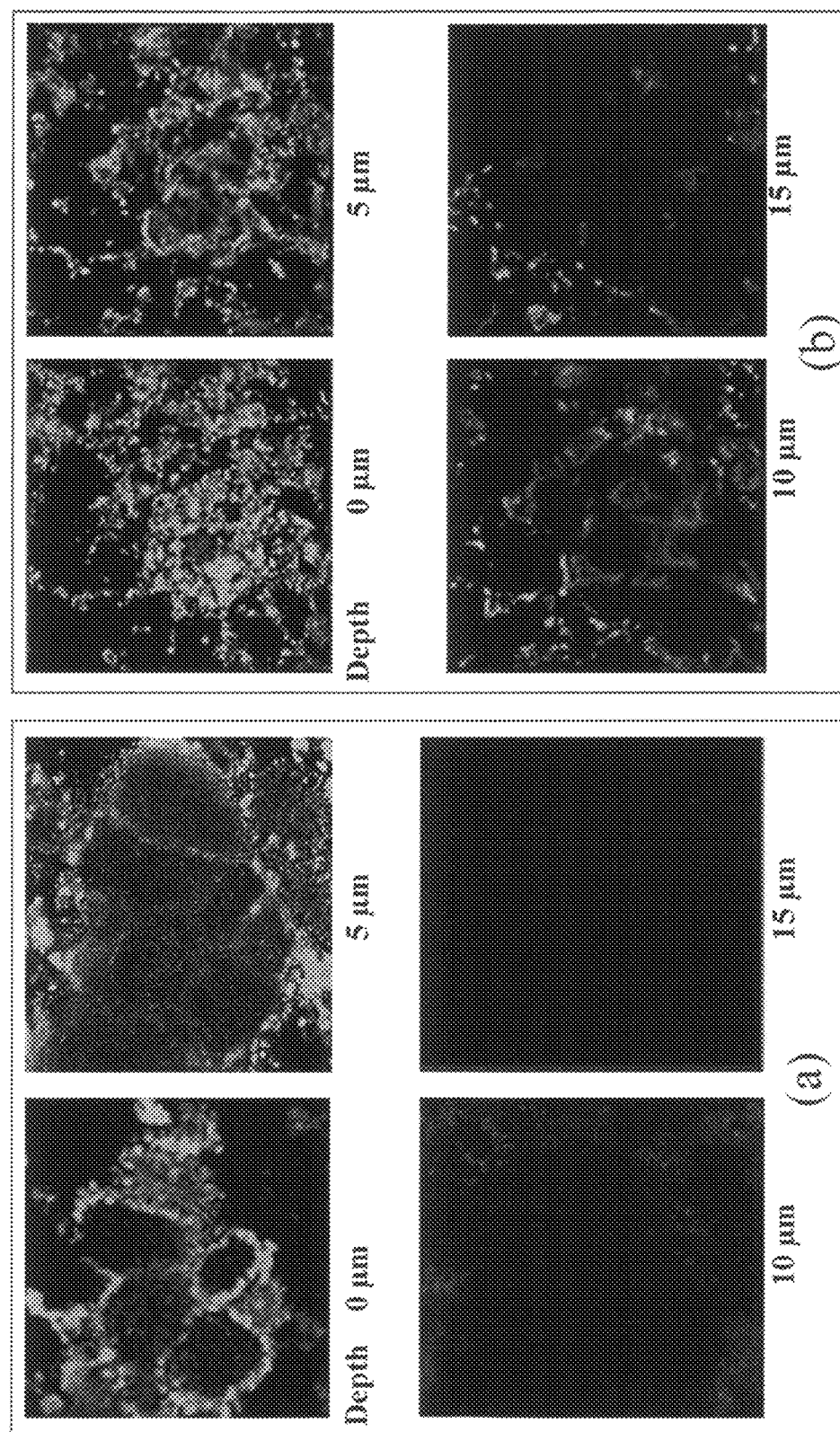
FIG. 7 shows fluorescence images (taken by an inversed confocal laser scanning microscope) of 4 optical sections of a Caco-2 cell monolayer that had been incubated with the fCS-γ-PGA nanoparticles with a positive surface charge (0.10% γ-PGA:0.20% CS) for (a) 20 min and (b) 60 min.

CLSM was used to visualize the transport of the fluorescence-labeled CS-γ-PGA (fCS-γ-PGA) nanoparticles across the Caco-2 cell monolayers. This non-invasive method allows for optical sectioning and imaging of the transport pathways across the Caco-2 cell monolayers, without disrupting their structures (J. Control. Release 1996; 39:131-138). FIGS. 7a and 7b show the fluorescence images of 4 optical sections of a Caco-2 cell monolayer that had been incubated with the fCS-γ-PGA nanoparticles having a positive surface charge (0.10% γ-PGA:0.20% CS, zeta potential: about 21 mV) for 20 and 60 min, respectively. As shown, after 20 min of incubation with the nanoparticles, intense fluorescence signals at intercellular spaces were observed at depths of 0 and 5 μm from the apical (upper) surface of the cell monolayer. The intensity of fluorescence became weaker at levels deeper than 10 μm from the apical surface of the cell monolayer and was almost absent at depths ≧15 μm (FIG. 7a).

After 60 minutes of incubation with the nanoparticles, the intensity of fluorescence observed at intercellular spaces was stronger and appeared at a deeper level than those observed at 20 min after incubation. These observations confirmed with our TEER results that the nanoparticles with a positive surface charge (CS dominated on the surface) were able to open the tight junctions between Caco-2 cells and allowed transport of the nanoparticles by passive diffusion via the paracellular pathways.

EXAMPLE No. 8

In Vivo Study with Fluorescence-Labeled Nanoparticles

Fluorescence (FITC)-labeled CS-γ-PGA (fCS-γ-PGA) nanoparticles were prepared for the confocal laser scanning microscopy (CLSM) study. After feeding rats with fCS-γ-PGA nanoparticles, the rats are sacrificed at a pre-determined time and the intestine is isolated for CLSM examination. The fluorescence images of the nanoparticles were clearly observed by CLSM that penetrates through the mouse intestine at appropriate time and at various depths from the inner surface toward the exterior surface of the intestine, including duodenum, jejunum, and ileum.

EXAMPLE No. 9

Insulin Loading Capacity in Nanoparticles

Fluorescence (FITC)-labeled γ-PGA was added into chitosan solution to prepare fluorescence (FITC)-labeled, insulin-loaded CS-γ-PGA nanoparticles for in vivo animal study with confocal laser scanning microscopy (CLSM) assessment and bioactivity analysis. The insulin-loaded CS-γ PGA nanoparticles are by using the ionic-gelation method upon addition of insulin mixed with γ-PGA solution into CS solution, followed by magnetic stirring in a container.

The nanoparticles with two insulin concentrations are prepared at a chitosan to γ-PGA ratio of 0.75 mg/ml to 0.167 mg/ml. Their particle size and zeta potential are shown in Table 2 below.

TABLE 2

| Insulin Conc. (mg/ml) (n = 5) | Mean Particle Size (nm) | Polydispersity Index (PI) | Zeta Potential (mV) |
|---|---|---|---|
| 0* | 145.6 ± 1.9 | 0.14 ± 0.01 | +32.11 ± 1.61 |
| 0.042 | 185.1 ± 5.6 | 0.31 ± 0.05 | +29.91 ± 1.02 |
| 0.083 | 198.4 ± 6.2 | 0.30 ± 0.09 | +27.83 ± 1.22 |

*control reference without insulin

Figure 11:
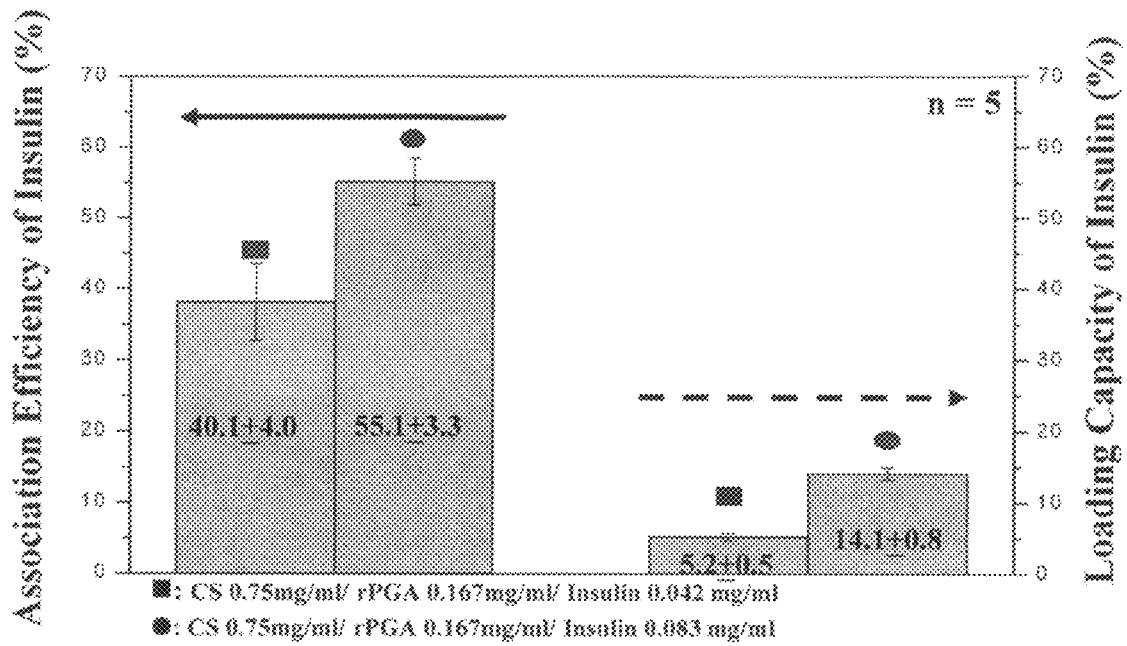
FIG. 11 shows loading capacity and association efficiency of insulin in nanoparticles of chitosan and γ-PGA.
Figure 12:
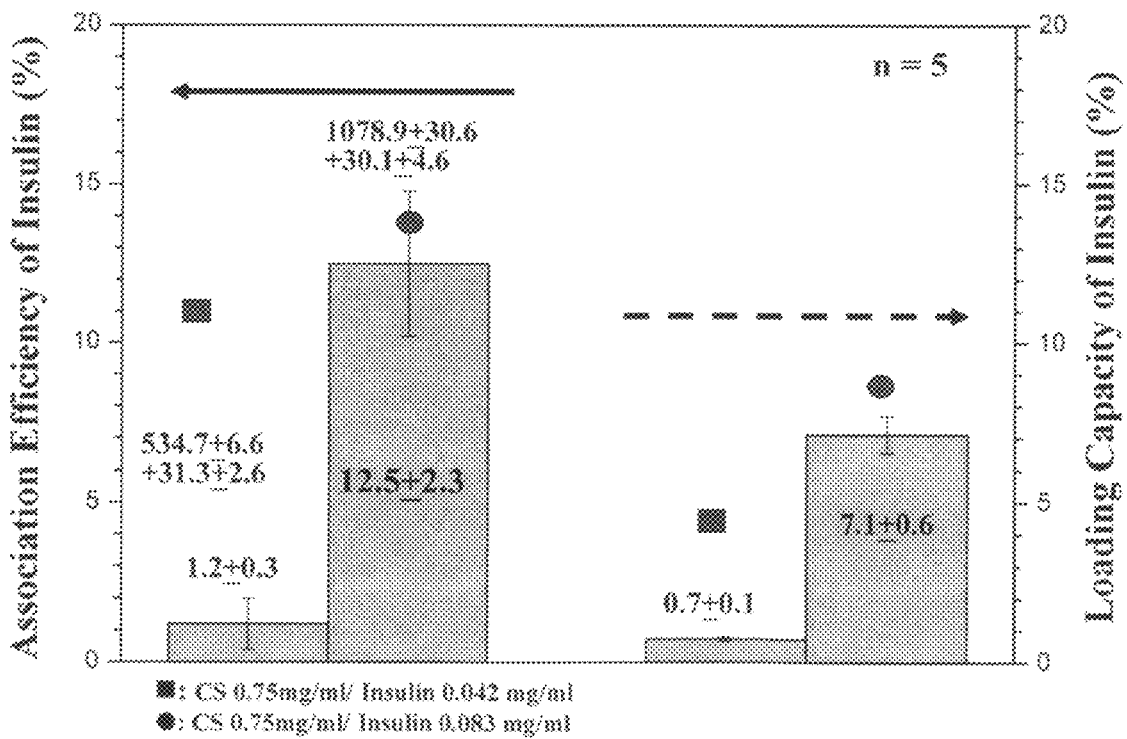
FIG. 12 shows loading capacity and association efficiency of insulin in nanoparticles of chitosan as reference.

Further, their association efficiency of insulin and loading capacity of insulin are analyzed, calculated and shown in FIGS. 11 and 12, according to the following formula:

$$\text{Insulin Association Efficiency } (AE\%) = \frac{\left(\begin{array}{c}\text{Total amount of insulin} - \\ \text{Insulin in supernatant}\end{array}\right)}{\text{Total amount of insulin}} \times 100\%$$

$$\text{Loading Capacity } (LC) = \frac{\left(\begin{array}{c}\text{Total amount of insulin} - \\ \text{Insulin in supernatant}\end{array}\right)}{\text{Weight of recovered particles}} \times 100\%$$

FIG. 11 shows loading capacity and association efficiency of insulin in nanoparticles of chitosan and γ-PGA, whereas FIG. 12 shows loading capacity and association efficiency of insulin in nanoparticles of chitosan alone (in absence of γ-PGA) as reference. The data clearly demonstrates that both the insulin loading capacity and insulin association efficiency are statistically higher for the nanoparticles with γ-PGA in the core. The AE (40~55%) and LC (5.0~14.0%) of insulin for CS-γPGA nanoparticles was obtained by using ionic-gelation method upon addition of insulin mixed with γ-PGA solution into CS solution, followed by magnetic stirring for nanoparticle separation. Some aspects of the invention relate to an oral dose of nanoparticles that effectively enhance intestinal or blood brain paracellular transport comprising a negative component (such as γ-PGA, heparin, or alginate) in the core and low molecular weight chitosan, wherein the chitosan dominates on a surface of the nanoparticles with positive charges. Alginate is non-biodegradable; however, it is stipulated that an alginate particle with about is kidney inert.

Calceti et al. reported an in vivo evaluation of an oral insulin-PEG delivery system (Eur J Pharma Sci 2004; 22:315-323). Insulin-PEG was formulated into mucoadhesive tablets constituted by the thiolated polymer poly(acrylic acid)-cysteine. The therapeutic agent was sustained released from these tablets within 5 hours. In vivo, by oral administration to diabetic mice, the glucose levels were found to decrease significantly over the time. Further, Krauland et al. reported another oral insulin delivery study of thiolated chitosan-insulin tablets on non-diabetic rats (J. Control. Release 2004, 95:547-555). The delivery tablets utilized 2-Iminothiolane covalently linked to chitosan to form chitosan-TBA (chitosan-4-thiobutylamidine) conjugate. After oral administration of chitosan-TBA-insulin tablets to non-diabetic conscious rats, the blood glucose level decreased significantly for 24 hours; supporting the observation of sustained insulin release of the presently disclosed nanoparticles herein through intestinal absorption. In a further report by Morcol et al. (Int. J. Pharm. 2004; 277:91-97), an oral delivery system comprising calcium phosphate-PEG-insulin-casein particles displays a prolonged hypoglycemic effect after oral administration to diabetic rats.

Pan et al. disclosed chitosan nanoparticles improving the intestinal absorption of insulin in vivo (Int J Pharma 2002; 249:139-147) with insulin-chitosan nanoparticles at a particle size of 250-400 nm, a polydispersity index smaller than 0.1, positively charged and stable. After administering the insulin-chitosan nanoparticles, it was found that the hypoglycemic was prolonged with enhanced pharmacological bioavailability. Their data confirmed our observation as shown in FIGS. 11 and 12; however, the insulin loading capacity and insulin association efficiency of the present invention are substantially higher for the chitosan-insulin nanoparticles with γ-PGA in the core.

EXAMPLE No. 10

Insulin Nanoparticle Stability

Figure 13:
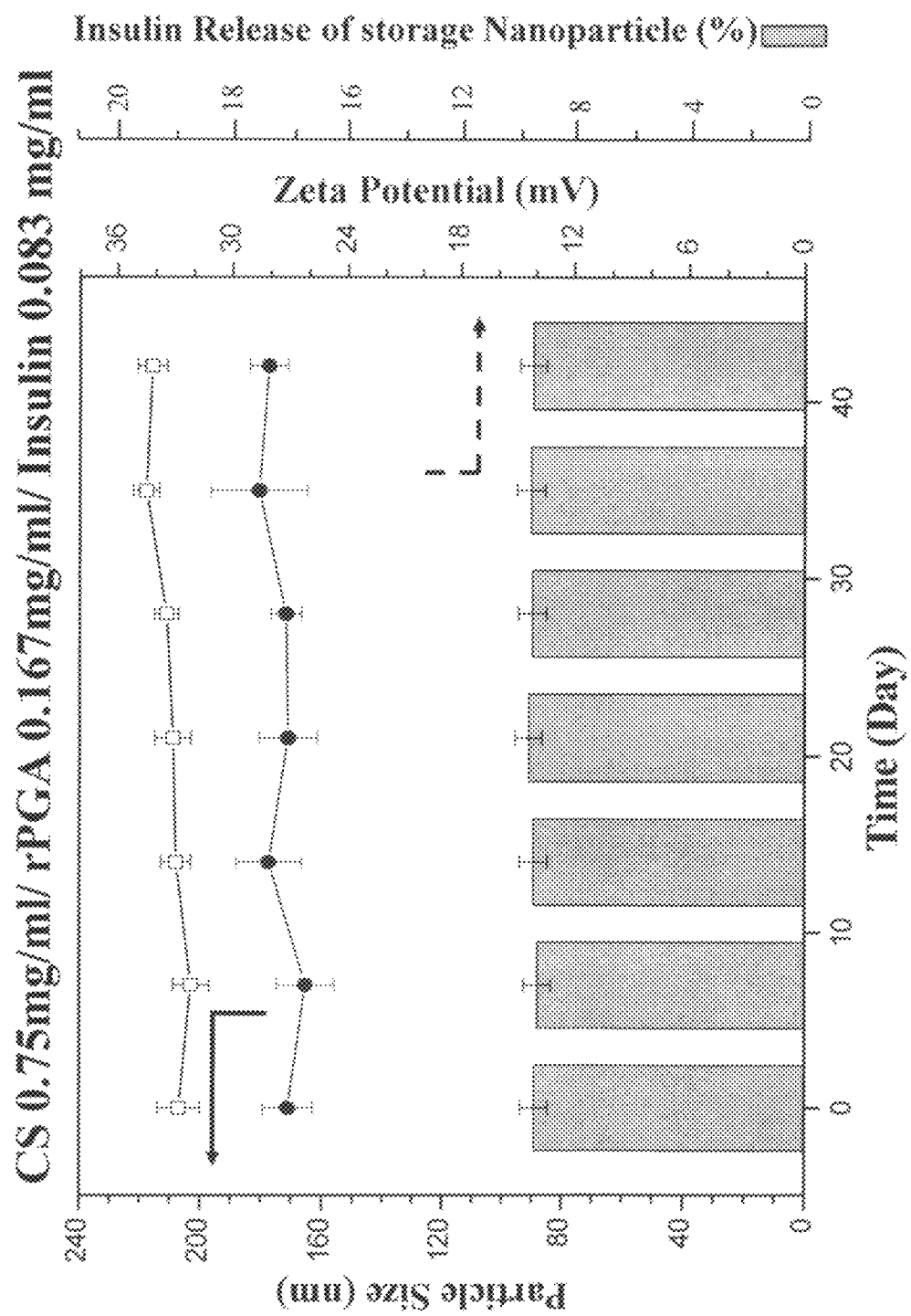
FIG. 13 shows the stability of insulin-loaded nanoparticles.

FIG. 13 shows the stability of insulin-loaded nanoparticles of the present invention with an exemplary composition of CS 0.75 mg/ml, γ-PGA 0.167 mg/ml, and insulin 0.083 mg/ml. The prepared insulin-loaded nanoparticles suspended in deionized water are stable during storage up to 40 days. First (in FIG. 13), the insulin content in the nanoparticle storage solution maintains at about a constant level of 9.5%. The nanoparticle stability is further evidenced by the substantially constant particle size at about 200 nm and substantially constant zeta potential of about +28 mV over the period of about 40 days. It is contemplated that the insulin-containing nanoparticles of the present invention would further maintain their biostability when formulated in a soft gelcap configuration that further isolates the nanoparticles from environmental effects, such as sunlight, heat, air conditions, and the like. Some aspects of the invention provide a gelcap pill containing a dosage of insulin nanoparticles effective amount of the insulin to treat or manage the diabetic patients, wherein the stability of the insulin-containing nanoparticles is at least 40 days, preferably more than 6 months, and most preferably more than a couple of years. By "effective amount of the insulin", it is meant that a sufficient amount of insulin will be present in the dose to provide for a desired therapeutic, prophylatic, or other biological effect when the compositions are administered to a host in the single dosage forms.

Thus, for convenient and effective oral administration, pharmaceutically effective amounts of the nanoparticles of this invention can be tabletted with one or more excipient, encased in capsules such as gel capsules, and suspended in a liquid solution and the like. The nanoparticles can be suspended in a deionized solution or the like for parenteral administration. The nanoparticles may be formed into a packed mass for ingestion by conventional techniques. For instance, the nanoparticles may be encapsulated as a "hard-filled capsule" or a "soft-elastic capsule" using known encapsulating procedures and materials. The encapsulating material should be highly soluble in gastric fluid so that the particles are rapidly dispersed in the stomach after the capsule is ingested. Each unit dose, whether capsule or tablet, will preferably contain nanoparticles of a suitable size and quantity that provides pharmaceutically effective amounts of the nanoparticles. One example is a size 0 gelatin capsule.

EXAMPLE No. 11

In Vitro Insulin Release Study

Figure 14:
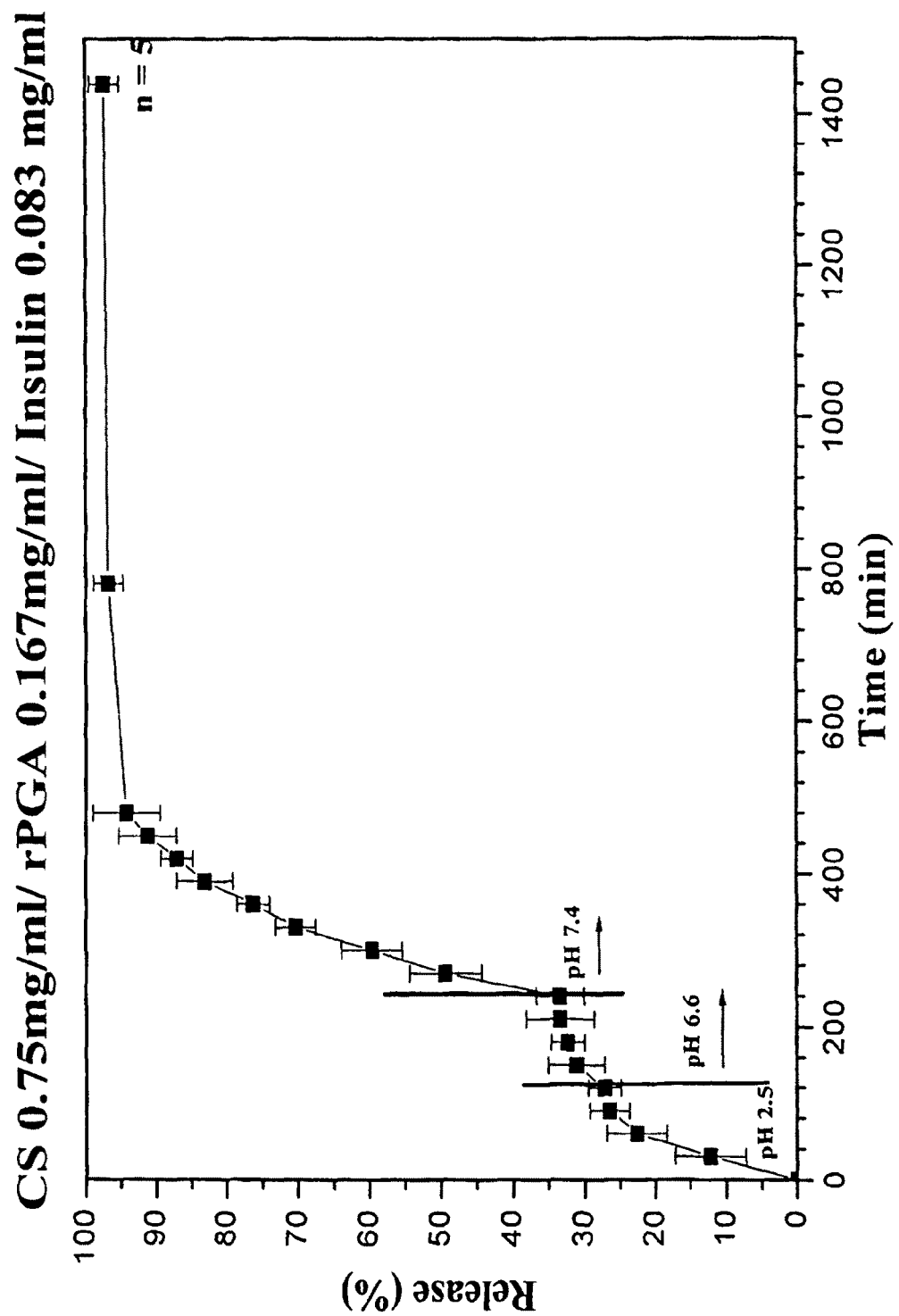
FIG. 14 show a representative in vitro study with insulin drug release profile in a pH-adjusted solution.

FIG. 14 show a representative protein drug (for example, insulin) release profile in a pH-adjusted solution for pH-sensitivity study with an exemplary composition of CS 0.75 mg/ml, γ-PGA 0.167 mg/ml, and insulin 0.083 mg/ml in nanoparticles. In one embodiment, the exemplary composition may include each component at a concentration range of ±10% as follows: CS 0.75 mg/ml (a concentration range of 0.67 to 0.83 mg/ml), γ-PGA 0.167 mg/ml (a concentration range of 0.150 to 0.184 mg/ml), and insulin 0.083 mg/ml (a concentration range of 0.075 to 0.091 mg/ml). First, solution of the insulin-loaded nanoparticles was adjusted to pH 2.5 to simulate the gastric environment in a DISTEK-2230A container at 37° C. and 100 rpm. Samples (n=5) were taken at a pre-determined particular time interval and the particle-free solution was obtained by centrifuging at 22,000 rpm for 30 minutes to analyze the free or released insulin in solution by HPLC. Until the free insulin content in the sample solution approaches about constant of 26% (shown in FIG. 14), the pH was adjusted to 6.6 to simulate the entrance portion of the intestine. The net released insulin during this particular time interval is about (from 26% to 33%) 7%. In other words, the nanoparticles are quite stable (evidenced by minimal measurable insulin in solution) for both the pH 2.5 and pH 6.6 regions. To further simulate the exit portion of the intestine, the insulin-containing nanoparticle solution is adjusted to pH 7.4. The remaining insulin (about 67%) is released from the nanoparticles. As discussed above, the insulin in nanoparticles would be more effective to penetrate the intestine wall in paracellular transport mode than the free insulin because of the nanoparticles of the present invention with chitosan at the outer surface (preferential mucosal adhesion on the intestinal wall) and positive charge (enhancing paracellular tight junction transport).

EXAMPLE No. 12

In Vivo Study with Insulin-Loaded Fluorescence-Labeled Nanoparticles

In the in vivo study, rats were injected with streptozotocin (STZ 75 mg/kg intraperitoneal) in 0.01M citrate buffer (pH 4.3) to induce diabetes rats. The blood from the rat's tail was analyzed with a commercially available glucometer for blood glucose. The blood glucose level on Wistar male rats at no fasting (n=5) is measured at 107.2±8.1 mg/dL for normal rats while the blood glucose level is at 469.7±34.2 mg/dL for diabetic rats. In the animal study, diabetic rats were fasting for 12 hours and subjected to four different conditions: (a) oral deionized water (DI) administration; (b) oral insulin administration at 30 U/kg; (c) oral insulin-loaded nanoparticles administration at 30 U/kg; and (d) subcutaneous (SC) insulin injection at 5 U/kg as positive control. The blood glucose concentration from rat's tail was measured over the time in the study.

Figure 15:
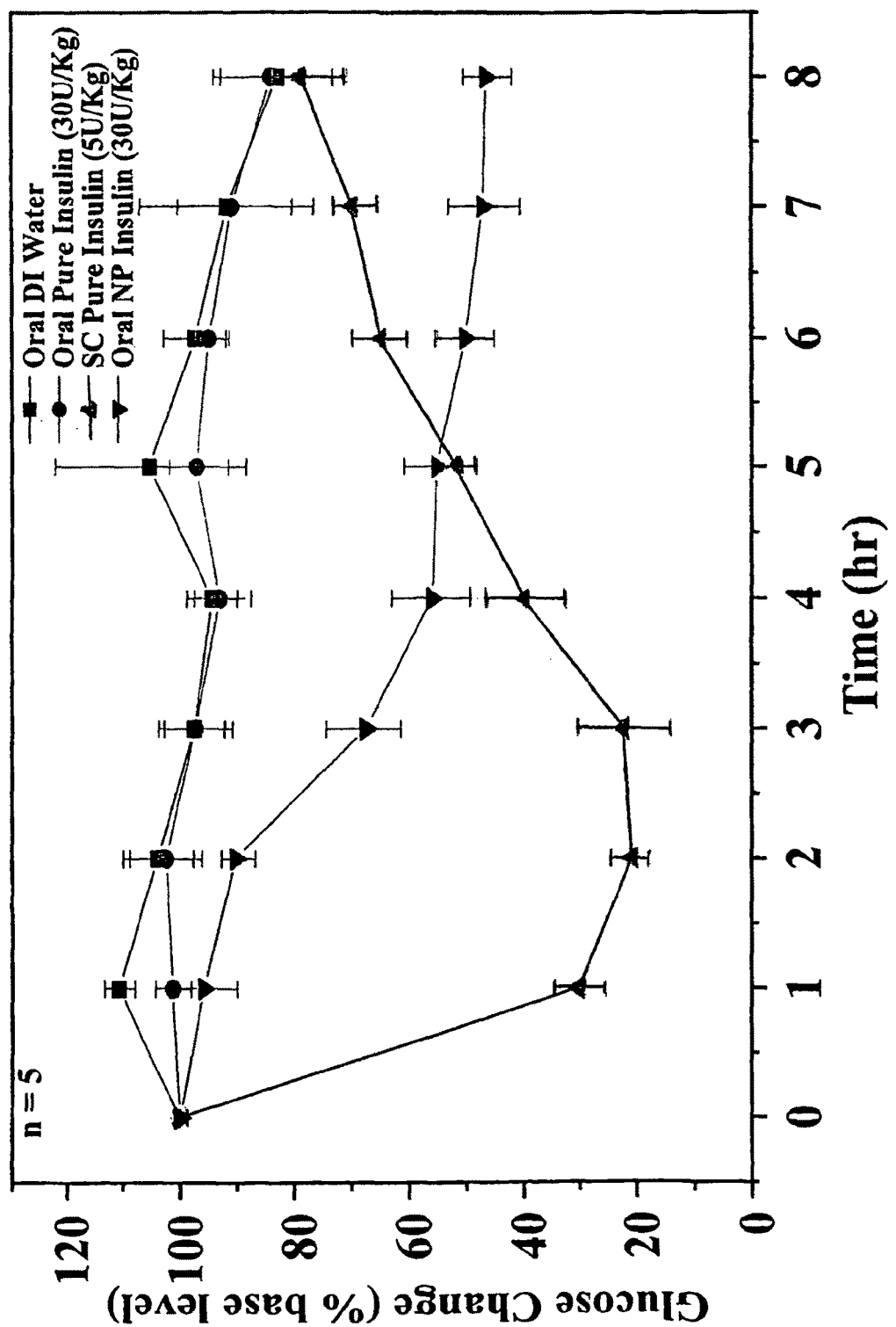
FIG. 15 show the bioavailability of insulin of orally administered insulin-loaded nanoparticles in diabetic rats.

FIG. 15 shows glucose change (hypoglycemic index) versus time of the in vivo animal study (n=5). The glucose change as a percentage of base lines for both oral DI administration and oral insulin administration over a time interval of 8 hours appears relatively constant within the experimental measurement error range. It is illustrative that substantially all insulin from the oral administration route has been decomposed in rat stomach. As anticipated, the glucose decrease for the SC insulin injection route appears in rat blood in the very early time interval and starts to taper off after 3 hours in this exemplary study. The most important observation of the study comes from the oral administration route with insulin-loaded nanoparticles. The blood glucose begins to decrease from the base line at about 2 hours after administration and sustains at a lower glucose level at more than 8 hours into study. It implies that the current insulin-loaded nanoparticles may modulate the glucose level in animals in a sustained or prolonged effective mode.

Some aspects of the invention relate to a novel nanoparticle system that is composed of a low-MW CS and γ-PGA with CS dominated on the surfaces being configured to effectively open the tight junctions between Caco-2 cell monolayers. The surface of the nanoparticles is characterized with a positive surface charge. In one embodiment, the nanoparticles of the invention enables effective intestinal delivery for bioactive agent, including peptide, polypeptide, protein drugs, other large hydrophilic molecules, and the like. Such polypeptide drugs can be any natural or synthetic polypeptide that may be orally administered to a human patient. Exemplary drugs include, but are not limited to, insulin; growth factors, such as epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; somatostatin; somatotropin; somatropin; somatrem; calcitonin; parathyroid hormone; colony stimulating factors (CSF); clotting factors; tumor necrosis factors: interferons; interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; LHRH; GHRH; tissue plasminogen activators; macrophage activator; chorionic gonadotropin; heparin; atrial natriuretic peptide; hemoglobin; retroviral vectors; relaxin; cyclosporin; oxytocin; vaccines; monoclonal antibodies; and the like; and analogs and derivatives of these compounds. The bioactive agent of the present invention may be selected from group consisting of oxytocin, vasopressin, adrenocorticotrophic hormone, prolactin, luliberin or luteinising hormone releasing hormone, growth hormone, growth hormone releasing factor, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines.

In another embodiment, the nanoparticles of the invention increase the absorption of bioactive agents across the blood brain barrier and/or the gastrointestinal barrier. In still another embodiment, the nanoparticles with chitosan at an outer layer and surface positive charge serve as an enhancer in enhancing paracellular drug (bioactive agent) transport of an administered bioactive agent when the bioactive agent and nanoparticles are orally administered in a two-component system, or orally administered substantially simultaneously.

Some aspects of the invention relate to a method of enhancing intestinal or blood brain paracellular transport of bioactive agents configured and adapted for delivering at least one bioactive agent in a patient comprising administering nanoparticles composed of γ-PGA and chitosan, wherein the nanoparticles are loaded with a therapeutically effective amount or dose of the at least one bioactive agent. The nanoparticle of the present invention is an effective intestinal delivery system for peptide and protein drugs and other large hydrophilic molecules. In a further embodiment, the bioactive agent is selected from the group consisting of proteins, peptides, nucleosides, nucleotides, antiviral agents, antineoplastic agents, antibiotics, and anti-inflammatory drugs. In a further embodiment, the bioactive agent is selected from the group consisting of calcitonin, cyclosporin, insulin, oxytocin, tyrosine, enkephalin, tyrotropin releasing hormone (TRH), follicle stimulating hormone (FSH), luteinizing hormone (LH), vasopressin and vasopressin analogs, catalase, superoxide dismutase, interleukin-II (IL2), interferon, colony stimulating factor (CSF), tumor necrosis factor (TNF) and melanocyte-stimulating hormone. In a further embodiment, the bioactive agent is an Alzheimer antagonist.

In a co-pending application, U.S. patent application Ser. No. 10/916,170 filed Aug. 11, 2004, it is disclosed that a biomaterial with free amino groups of lysine, hydroxylysine, or arginine residues within biologic tissues is crosslinkable with genipin, a crosslinker (Biomaterials 1999; 20:1759-72).

It is also disclosed that the crosslinkable biomaterial may be crosslinked with a crosslinking agent or with light, such as ultraviolet irradiation, wherein the crosslinkable biomaterial may be selected from the group consisting of collagen, gelatin, elastin, chitosan, NOCC (N, O, carboxylmethyl chitosan), fibrin glue, biological sealant, and the like. Further, it is disclosed that a crosslinking agent may be selected from the group consisting of genipin, its derivatives, analog (for example, aglycon geniposidic acid), stereoisomers and mixtures thereof. In one embodiment, the crosslinking agent may further be selected from the group consisting of epoxy compounds, dialdehyde starch, glutaraldehyde, formaldehyde, dimethyl suberimidate, carbodiimides, succinimidyls, diisocyanates, acyl azide, reuterin, ultraviolet irradiation, dehydrothermal treatment, tris(hydroxymethyl)phosphine, ascorbate-copper, glucose-lysine and photo-oxidizers, and the like.

In one embodiment, it is disclosed that loading drug onto a chitosan-containing biological material crosslinked with genipin or other crosslinking agent may be used as biocompatible drug carriers for drug slow-release or sustained release. Several biocompatible plastic polymers or synthetic polymers have one or more amine group in their chemical structures, for example poly(amides) or poly(ester amides). The amine group may become reactive toward a crosslinking agent, such as glutaraldehyde, genipin or epoxy compounds of the present invention. In one embodiment, the nanoparticles comprised of crosslinkable biomaterial is crosslinked, for example up to about 50% degree or more of crosslinking, preferably about 1 to about 20% degree of crosslinking of the crosslinkable components of the biomaterial, enabling sustained biodegradation of the biomaterial and/or sustained drug release.

By modifying the chitosan structure to alter its charge characteristics, such as grafting the chitosan with methyl, alkyl (for example, ethyl, propyl, butyl, isobutyl, etc.), polyethylene glycol (PEG), or heparin, the surface charge density (zeta potential) of the CS-γ PGA nanoparticles may become more pH resistant or hydrophilic.

By way of illustration, trimethyl chitosan chloride might be used in formulating the CS-γ PGA nanoparticles for maintaining its spherical biostability at a pH lower than pH 2.5, preferably at a pH as low as 1.0. Some aspects of the invention provide a drug-loaded chitosan-containing biological material crosslinked with genipin or other crosslinking agent as a biocompatible drug carrier for enhancing biostability at a pH lower than pH 2.5, preferably within at a pH as low as 1.0.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A pharmaceutical composition of nanoparticles for vaccine delivery comprising:
    (a) a vaccine,
    (b) a low molecular weight chitosan, and
    (c) a polyglutamic acid or salt thereof, wherein said nanoparticles have a net positively charged surface.

2. The pharmaceutical composition of claim 1, wherein said polyglutamic acid is γ-polyglutamic acid (γ-PGA) or α-polyglutamic acid (α-PGA).

3. The pharmaceutical composition of claim 1, wherein said nanoparticles are further encapsulated in a capsule.

4. The pharmaceutical composition of claim 1, wherein the low molecular weight chitosan has a molecular weight of 80 kDa.

5. The pharmaceutical composition of claim 1, wherein the low molecular weight chitosan has a molecular weight of 40 kDa.

6. The pharmaceutical composition of claim 1, wherein the low molecular weight chitosan is trimethyl chitosan, N,O-carboxylmethyl chitosan, or chitosan modified with a side chain selected from the group consisting of alkyl group and polyethylene glycol.

7. The pharmaceutical composition of claim 1, wherein the composition is in a tablet form with one or more excipients.

8. The pharmaceutical composition of claim 1, wherein said vaccine is a prophylactic vaccine.

9. The pharmaceutical composition of claim 1, wherein said vaccine is a therapeutic vaccine.

10. The pharmaceutical composition of claim 1, wherein the composition is formulated for oral administration.

11. The pharmaceutical composition of claim 1, wherein the composition is formulated for parenteral administration.

12. The pharmaceutical composition of claim 1, wherein said nanoparticles are prepared via a simple and mild ionic-gelation method.

13. The pharmaceutical composition of claim 1, wherein said nanoparticles are crosslinked with a crosslinking agent or with infrared irradiation.

14. The pharmaceutical composition of claim 13, wherein a degree of crosslinking of said nanoparticles is less than 50%.

15. The pharmaceutical composition of claim 13, wherein a degree of crosslinking of said nanoparticles is ranged between 1% and 20%.

* * * * *